(12) United States Patent
Rasochova et al.

(10) Patent No.: US 8,569,015 B2
(45) Date of Patent: Oct. 29, 2013

(54) RPA OPTIMIZATION

(75) Inventors: Lada L. Rasochova, Del Mar, CA (US); Philip P. Dao, Lausanne (CH); Jamie P. Phelps, Aurora, CO (US)

(73) Assignee: Pfenex Inc., San Diego, CA (US)

( * ) Notice: Subject to any disclaimer, the term of this patent is extended or adjusted under 35 U.S.C. 154(b) by 1170 days.

(21) Appl. No.: 11/809,100

(22) Filed: May 30, 2007

(65) Prior Publication Data

US 2008/0058262 A1   Mar. 6, 2008

Related U.S. Application Data

(60) Provisional application No. 60/809,536, filed on May 30, 2006.

(51) Int. Cl.
*C12P 21/06* (2006.01)
*C12N 15/74* (2006.01)

(52) U.S. Cl.
USPC .......................................... 435/69.1; 435/471

(58) Field of Classification Search
None
See application file for complete search history.

(56) References Cited

U.S. PATENT DOCUMENTS

| | | | |
|---|---|---|---|
| 4,751,180 A | 6/1988 | Cousens et al. | |
| 4,935,233 A | 6/1990 | Bell et al. | |
| 6,770,479 B1 * | 8/2004 | Lee et al. | 435/456 |
| 6,828,124 B2 | 12/2004 | Bogosian et al. | |
| 6,924,365 B1 | 8/2005 | Miller et al. | |
| 7,261,900 B2 * | 8/2007 | Leppla et al. | 424/246.1 |
| 2004/0009945 A1 | 1/2004 | Lee et al. | |

FOREIGN PATENT DOCUMENTS

| | | |
|---|---|---|
| EP | 2021490 | 3/2008 |
| EP | 2363495 | 9/2011 |
| WO | WO 02/10411 A2 | 2/2002 |
| WO | WO 2005/034841 A2 | 4/2005 |
| WO | 2005/067478 A2 | 7/2005 |
| WO | WO 2008/027099 | 6/2008 |

OTHER PUBLICATIONS

GenBank AAA22637.1 (last viewed on Mar. 27, 2010).*
Ochsner et al., Production of *Pseudomonas aeruginosa* Rhamnolipid Biosurfactants in Heterologous Host., Applied and Environmental Microbiology, 1995, vol. 61, pp. 3503-3506.*
Landry et al., Safety evaluation of an a-amylase enzyme preparation derived from teh archaeal order Thermococcales as expressed in *Pseudomonas fluorescens* biovar I., Regulatory Toxicology and Pharmacology, 2003, vol. 37, p. 149-168.*
Peng et al., A endotoxin encoded in *Pseudomonas fluorescens* displys a high degree of insecticidal activity., Appl Microbiol Biotechnol, 2003, vol. 63, pp. 300-306.*
Silby et al., IVET experiments in *Pseudomonas fluorescens* reveal cryptic promoters at loci associated with recognizable overlapping genes., Microbiology, 2004, vol. 150, pp. 518-520.*
Squires et al. (*Pseudomonas fluorescens*—A robust manufacturing platform, Biotechnology, Reprinted from 2004).*
Altschul, Stephen F., et al., Basic Alignment Search Tool, J. Mol. Biol., 1990, pp. 403-410, vol. 215.

(Continued)

*Primary Examiner* — Alexander Kim
(74) *Attorney, Agent, or Firm* — Wilson, Sonsini, Goodrich & Rosati

(57) ABSTRACT

An optimized synthetic polynucleotide encoding a *Bacillus anthracis* protective antigen and an anthrax vaccine based on the encoded protective antigen. Furthermore, heterologous expression in a host *Pseudomonas fluorescens* bacteria of an optimized polynucleotide sequence encoding a *Bacillus anthracis* protective antigen.

4 Claims, 10 Drawing Sheets

(56) References Cited

OTHER PUBLICATIONS

Altschul, Stephen F., et al., Gapped Blast and PSI Blast: a New Generation of Protein Database Search Programs, Nucleic Acids Research, 1997, pp. 3389-3402, vol. 25, No. 17, Oxford University Press.

Chew, Lawrence C., et al., *Psuedomonas fluorescens*, Production of Recombinant Proteins. Novel Microbial and Eucaryotic Expression Systems, Chapter 3, Gelliser, Gerd ed., 2005, pp. 45-66.

Clark-Curtiss, Josephine, et al., Analysis of Recombinant DNA, Methods in Enzymology, 1983, pp. 347-362, vol. 101, Academic Press, Inc.

Daly, Richard, et al., Expression of Heterologous Proteins in *Pichia pastoris*: a Useful Experimental Tool in Protein Engineering and Production, Journal of Molecular Recognition, 2005, pp. 119-138, vol. 18, John Wiley & Sons, Ltd.

Davis, Bernard D., et al., Mutants of *Escherichia coli* Requiring Methionine or Vitamin B(12), J. Bact., 1950, pp. 17-28, vol. 60.

Gene Design to Improve Heterologous Protein Expression, GenScript Corporation, web page: www.genscript.com/gene_design.html, retrieved Nov. 26, 2007.

Doudoroff, M., et al., Gram-Negative Aerobic Rods and Cocci, Bergey's Manual of Determinative Bacteriology, 1974, pp. 217-289, edited by Buchanan and Gibbons.

Griswold, Karl E., Effects of Codon Usage Versus Putative 5'-mRNA Structure on the Expression of Fusarium Solani Cutinase in the *Escherichia coli* Cytoplasm, Protein Expression and Purification, 2003, pp. 134-142, vol. 27, Elsevier Science (USA).

Hepler, Robert W., A Recombinant 63-kDa Form of *Bacillus anthracis* Protective Antigen Produced in the Yeast *Saccharomyces cerevisiae* Provides Protection in Rabbit and Primate Inhalational Challenge Models of Anthrax Infection, Vaccine, 2006, pp. 1501-1514, vol. 24, Elsevier.
Higgins, Desmond G., et al., Fast and Sensitive Multiple Sequence Alignments on a Microcomputer, Cabios Communications, 1989, pp. 151-153, vol. 5, No. 2, IRL Press.
Morrison, D.A., Transformation in *Escherichia coli*: Cryogenic Preservation of Competent Cells, Journal of Bacteriology, Oct. 1977, pp. 349-351, vol. 132, No. 1, American Society for Microbiology.
Maratea, Denise, et al., Deletion and Fusion Analysis of the Phage øX174 Lysis Gene, 1985, pp. 39-46, vol. 40, Elsevier Press.
Myers, E. W., et al Optimal Alignments in Linear Space, CABIOS, 1988, pp. 11-17, vol. 4, No. 1, IRL Press . Limited, Oxford England.
Needleman, Saul B., et al., A General Method Applicable to the Search for Similarities in the Amino Acid Sequence of two Proteins, J. Mol. Biol., 1970, pp. 443-453, vol. 48.
Pearson, William R., et al., Improved Tools for Biological Sequence Comparison, Proc. Natl. Acad. Sci., Apr. 1988, pp. 2444-2448, vol. 85.
Retallack, Diane, et al., *Pseudomonas fluorescens* —a Robust Expression Platform for Pharmaceutical Protein Production, Microbial Cell Factories, 2006, p. S28, Vol. 2, Suppl. 1.
Riesenberg, D., et al., High Cell Density Cultivation of *Escherichia coli* at Controlled Specific Growth Rate, Journal of Biotechnology, 1991, pp. 17-28, vol. 20, Elsevier Science Publishers, B.V.
Robinson, D.F., Comparison of Labeled Trees with Valency Three, Journal of Combinatorial Theory, 1971, pp. 105-119, vol. 11.
Saitou, Naruya, et al., The Neighbor-Joining Method: A New Method for Reconstructing Phylogenetic Trees, Mol. Biol. Evol., 1987, pp. 406-425, vol. 4, No. 4, The University of Chicago.
Sorenson, Hans Peter, Production of Recombinant Thermostable Proteins Expressed in *Escherichia coli*: Completion of Protein Synthesis is the Bottleneck, Journal of Chromatography B, 2003, pp. 207-214, vol. 786.
Smith, Temple F., et al., Comparison of Biosequences, Advances in Applied Mathematics, 1981, pp. 482-489, vol. 2, Academic Press, Inc.
Wilbur, W.J., and Lipman, D. J., Rapid Similarity Searches of Nucleic Acid and Protein Data Banks, Proc. Natl. Acad. Sci. USA, 1983, pp. 726-730, vol. 80, Biochemistry.
Vervoort, Elisa B., et al., Optimizing Heterologous Expression in Dictyostelium: Importance of 5' Codon Adaptation, Nucleic Acids Research, 2000, pp. 2069-2074, vol. 28, No. 10.
PCT International Search Report for International Patent Application PCT/US2007/012842 (WO 2008/027099), mailed Nov. 10, 2008.
Murphy, John R., et al., "Genetic construction, expression, and melanoma-selective cytotoxicity of a diphtheria toxin-related alpha-melanocyte-stimulating hormone fusion protein," Genetics, Proc. Natl. Acad. Sci. USA, vol. 83, pp. 8258-8262, Nov. 1986.
Haas, Jurgen, et al., Codon Usage Limitation in the Expression of HIV-1 Envelope Glycoprotein, Current Biology, 1996, pp. 315-324, vol. 6, No. 3, Current Biology Ltd.
Hein, Jotun, Unified Approach to Alignment and Phylogenies, Methods in Enzymology, 1990, pp. 626-645, vol. 183, Academic Press, Inc.
Yang, Te-Tuan, et al., Optimized Codon Usage and Chromophore Mutations Provide Enhanced Sensitivity with the Green Fluorescent Protein, Nucleic Acids Research, 1996, pp. 4592-4593, vol. 24, No. 22, Oxford University Press.
Buchanan and Gibbions (eds.), "Gram-Negative Aerobic Rods and Cocci." Bergey's Manual of Determinative Bacteriology, pp. 217-289 (8th ed., 1974)(The Williams & Wilkins Co., Baltimore, MD, USA).
Dayhoff., M.O. et al., A model of Evotutionary Change in Proteins, Atlas of Protein Sequence and Structure, vol. 5, Supplement 3, Chapter 2, Margaret O. Dayhoff, ed., pp. 345-358, National Biomed Research Foundation, Washington, D.C. (1978).
Jung: Continuous production of recombinant interferon-alpha in *Escherichia coli* via the depression of trp promototer using casamino acid, Process Biochemistry, vol. 41, Apr. 2006, pp. 809-814.
Saraswat, et al., "Effect of Specific production rate of recombinant protein on multimerization of plasmid vector and gene expression level." FEMS Microbiology Letters, vol. 179, 1999, pp. 367-373.
EP11159904.9 European Search Report dated Aug. 9, 2011.
Gwinn et al., "Scalable purification of *Bacillus anthracis* protective antigen from *Escherichia coli*," Protein Expression and Purification 45:30-36 (2006).
Laird et al., "Production and purification of *Bacillus anthracis* protective antigen from *Escherichia coli*," Protein Expression and Purification 38:145-152 (2004).

* cited by examiner

RPA OPTIMIZATION

CROSS REFERENCE TO RELATED APPLICATION

This application claims the benefit of U.S. provisional patent application, Ser. No. 60/809,536, filed May 30, 2006.

STATEMENT OF GOVERNMENT SUPPORT

This application was made with Government support under grant number. 1-U01-AI054641-01 from the National Institutes of Health, National Institute of Allergy and Infectious Disease (NIAID. The government has certain rights to this invention.

REFERENCE TO SEQUENCE LISTING SUBMITTED ELECTRONICALLY

The instant application contains a Sequence Listing which has been submitted in ASCII format via EFS-Web and is hereby incorporated by reference in its entirety. Said ASCII copy, created on Dec. 3, 2010, is named 94725201.txt and is 43,572 bytes in size.

FIELD OF THE INVENTION

The present invention relates generally to a *Bacillus anthracis* protective antigen-based anthrax vaccine. In particular, the invention relates to heterologous expression bacteria of an optimized polynucleotide sequence encoding a *Bacillus anthracis* protective antigen in a bacterial host.

BACKGROUND OF THE INVENTION

Anthrax is a zoonotic disease whose etiologic agent is a gram-positive sporulating bacterium, *B. anthracis*. Human beings can acquire it via infected animals or contaminated animal products. The etiologic agent of anthrax (*Bacillus anthracis*) is a potential threat as an agent of biowarfare or bioterrorism because exposure to aerosolized *B. anthracis* spores can be lethal to mammals, such as humans. Vaccination is currently thought of as the most effective way to protect individuals and entire populations from an anthrax infection. Virulence of *B. anthracis* is due to two major antigens: the antiphagocytic capsular antigen and the anthrax toxin. The antiphagocytic capsular antigen does not protect against anthrax infection. However, the anthrax toxin is highly immunogenic and is the basis for successful anthrax vaccines.

The anthrax toxin has three peptide components: the protective antigen (PA; 83 kDa), the lethal factor (LF; 90 kDa), and the edema factor (EF; 89 kDa). The EF is a calcium-calmodulin-dependent adenylate cyclase believed to cause the edema associated with anthrax infection and to prevent immune cells from ingesting and degrading the bacteria. The LF is a cell-type specific metalloprotease that cleaves mitogen-activated protein kinase-kinases and several peptide hormones. It causes macrophage cell death and release of toxic substances (e.g., those associated with septic shock such as TNF-α and IL-1). LF is the major virulence factor associated with anthrax toxicity and is responsible for systemic shock and death. The genes for all three peptide components have been cloned and sequenced. No single anthrax toxin component alone is toxic; however, a combination of PA and either LF or EF leads to infection and pathogenesis. During the *B. anthracis* infectious process, PA83 binds to a ubiquitous cell surface receptor. One or more proteases including a furin-like protease is present at the exterior of cells and plays a role in the proteolytic activation of receptor bound PA. PA is secreted as an 83 kDa monomeric polypeptide. Monomeric PA binds to a mammalian cell surface receptor and is proteolytically cleaved. The C-terminal 63 kDa fragment (PA63) remains bound to the cell and the N-terminal 20 kDa (PA20) dissociates from PA63. The cleavage generates PA63 and exposes a high affinity site on PA to which LF/EF can bind competitively. PA63 heptamerizes and inserts into the membrane as a pore upon exposure to acidic pH after receptor mediated endocytosis. The PA63 oligomer translocates EF/LF into the cytosol. The fourth domain of PA (PA-D4) is responsible for initial binding of the anthrax toxin to the cellular receptor, and is an attractive target for vaccines.

Some studies have illustrated that both monoclonal and polyclonal antibodies to PA may neutralize the anthrax toxin and function to provide immunity against the pathogen. One such current anthrax vaccine includes an aluminum hydroxide-adsorbed cell-free filtrate of cultures of a noncapsulating nonproteolytic strain of *B. anthracis* (Anthrax Vaccine Absorbed, AVA) in which PA is the major protective component.

Although these vaccines have proven efficacious, they possess certain limitations. Namely, vaccine quality and efficacy vary among production batches depending on the levels of PA production and the presence of impurities, such as traces of active toxin components LF and EF, which can produce serious side effects in a subject.

Culture supernatants of *B. anthracis* have been the major source for purifying PA. However, working with *B. anthracis* cultures requires expensive biosafety level-3 containment facilities. Additionally, PA preparation from *B. anthracis* is often contaminated with LF or EF. Heterologous expression of PA from other hosts, such as *Bacillus subtilis*, has been attempted in the past, but with difficulty. PA production from *B. subtilis* or a protease deficient *B. subtilis* host yields only limited quantities of PA, thus increasing the costs of additional production batches. Similarly, Baculovirus vectors have also been used to express PA in insect cells; however, purification is not feasible due to low PA yields and the persistence of undesirable impurities. PA has also been expressed in *Escherichia coli*, however, a low yield was observed and the protein was insoluble when expressed in the cytoplasm. Heterologous expression in *E. coli* used codon optimized recombinant PA (rPA) and the protein was targeted into the periplasm of the expression host.

BRIEF SUMMARY OF THE INVENTION

The present invention includes a synthetic polynucleotide having a nucleotide sequence encoding a *B. anthracis* protective antigen protein, wherein the synthetic polynucleotide sequence has been optimized for heterologous expression in a bacterial host cell such as *P. fluorescens*.

The present invention also provides a method of producing a recombinant *Bacillus anthracis* protective antigen protein in the cytoplasm and periplasm of the bacterial cell including optimizing a synthetic polynucleotide sequence for heterologous expression in a bacterial host, wherein the synthetic polynucleotide comprises a nucleotide sequence encoding a *Bacillus anthracis* protective antigen protein. The method also includes ligating the optimized synthetic polynucleotide sequence into an expression vector and transforming the host bacteria with the expression vector. The method additionally including culturing the transformed host bacteria in a suitable culture media appropriate for the expression of the *Bacillus*

*anthracis* protective antigen protein and isolating the *Bacillus anthracis* protective antigen protein. The bacteria host selected can be *Pseudomonas fluorescens*.

Other embodiments of the present invention include methods of optimizing synthetic polynucleotide sequences for heterologous expression in a host cell by identifying and removing rare codons from the synthetic polynucleotide sequence that are rarely used in the host. Furthermore, these methods can include identification and removal of putative internal ribosomal binding site sequences as well as identification and removal extended repeats of G or C nucleotides from the synthetic polynucleotide sequence. The methods can also include identification and minimization of protective antigen protein secondary structures in the RBS and gene coding regions, as well as removing undesirable enzyme-restriction sites from the synthetic polynucleotide sequences.

Embodiments of the present invention also include vaccines comprising a recombinant *Bacillus anthracis* protective antigen protein, wherein the recombinant *Bacillus anthracis* protective antigen protein is encoded by a synthetic polypeptide that has been optimized for heterologous expression in a bacterial host. The bacterial host can be *Pseudomonas fluorescens*.

DETAILED DESCRIPTION OF THE INVENTION

Figure 1:
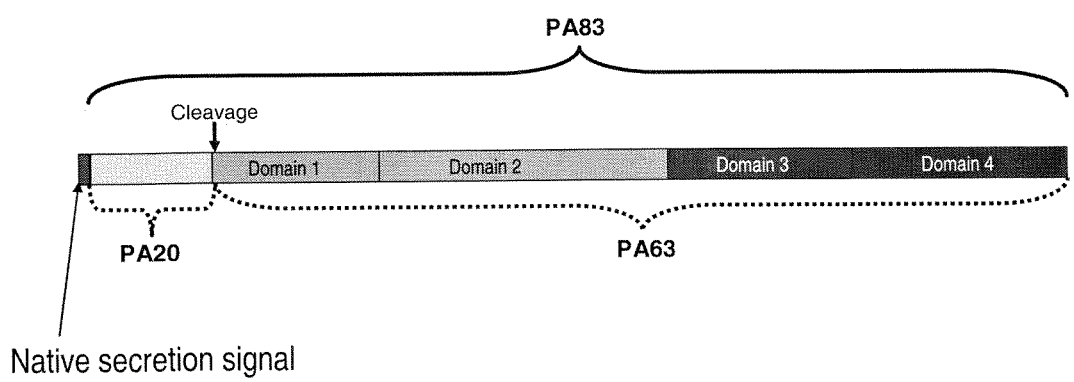
FIG. 1 illustrates the PA83 protein with indicated domains.

The present invention is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention relates to synthetic polynucleotide sequences that encode for a recombinant *B. anthracis* protective antigen (rPA) protein that can be used for prophylactic immunization against anthrax infections. Embodiments of the present invention also provide for the heterologous expression of a synthetic polynucleotide in a bacterial host. Other embodiments include a heterologous expression of a synthetic polynucleotide in *Pseudomonas fluorescens* or *E. coli*. Additional embodiments of the present invention also include optimized polynucleotide sequences encoding a recombinant *Bacillus anthracis* rPA that can be expressed using a heterologous *P. fluorescens*-based expression system. Another embodiment of the present invention also includes a heterologous expression of a synthetic polynucleotide in the cytoplasm of *Pseudomonas fluorescens*. Additional embodiment of the present invention also includes a heterologous expression of a synthetic polynucleotide in the periplasm of *Pseudomonas fluorescens*. These optimized polynucleotide sequences can provide for a high yield of soluble rPA.

In heterologous expression systems, optimization steps may improve the ability of the host to produce the foreign protein. Protein expression is governed by a host of factors including those that affect transcription, mRNA processing, and stability and initiation of translation. The polynucleotide optimization steps may include steps to improve the ability of the host to produce the foreign protein as well as steps to assist the researcher in efficiently designing expression constructs. Optimization strategies may include, for example, the modification of translation initiation regions, alteration of mRNA structural elements, and the use of different codon biases. The following paragraphs discuss potential problems that may result in reduced heterologous protein expression, and techniques that may overcome these problems.

One area that can result in reduced heterologous protein expression is a rare codon-induced translational pause. A rare codon-induced translational pause includes the presence of codons in the polynucleotide of interest that are rarely used in the host organism may have a negative effect on protein translation due to their scarcity in the available tRNA pool. One method of improving optimal translation in the host organism includes performing codon optimization which can result in rare host codons being removed from the synthetic polynucleotide sequence.

Another area that can result in reduced heterologous protein expression is by alternate translational initiation. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes eliminating putative internal RBS sequences from an optimized polynucleotide sequence.

Another area that can result in reduced heterologous protein expression is through repeat-induced polymerase slippage. Repeat-induced polymerase slippage involves nucleotide sequence repeats that have been shown to cause slippage or stuttering of DNA polymerase which can result in frame-shift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Another area that can result in reduced heterologous protein expression is through interfering secondary structures. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

Another area that can effect heterologous protein expression are restriction sites: By removing restriction sites that could interfere with subsequent sub-cloning of transcription units into host expression vectors a polynucleotide sequence can be optimized.

Figure 2:
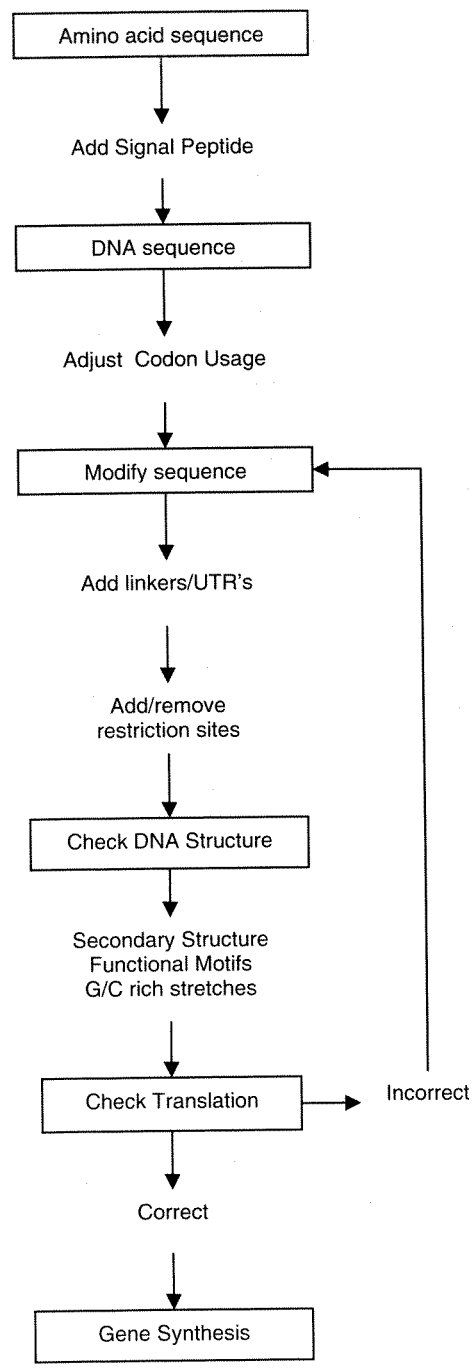
FIG. 2 illustrates a flow diagram showing steps that can be used during optimization of a synthetic polynucleotide sequence.
Figure 3:
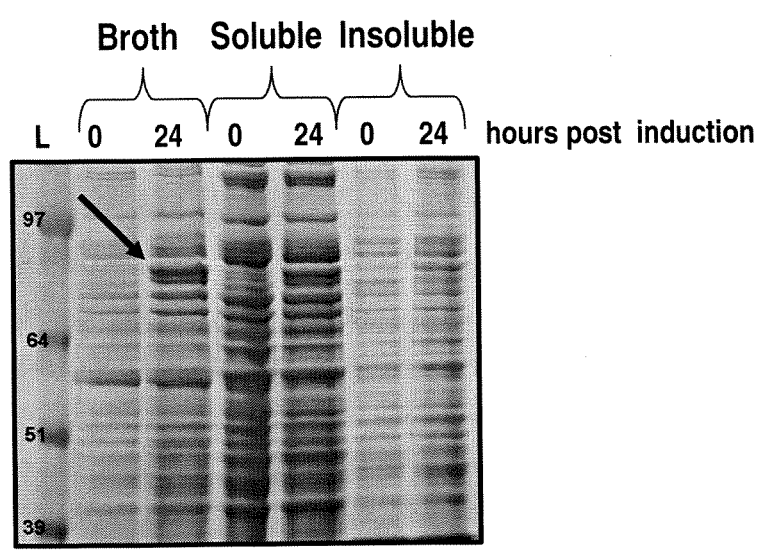
FIG. 3 illustrates expression of rPA83 containing the native signal in *P. fluorescens*.
Figure 4:
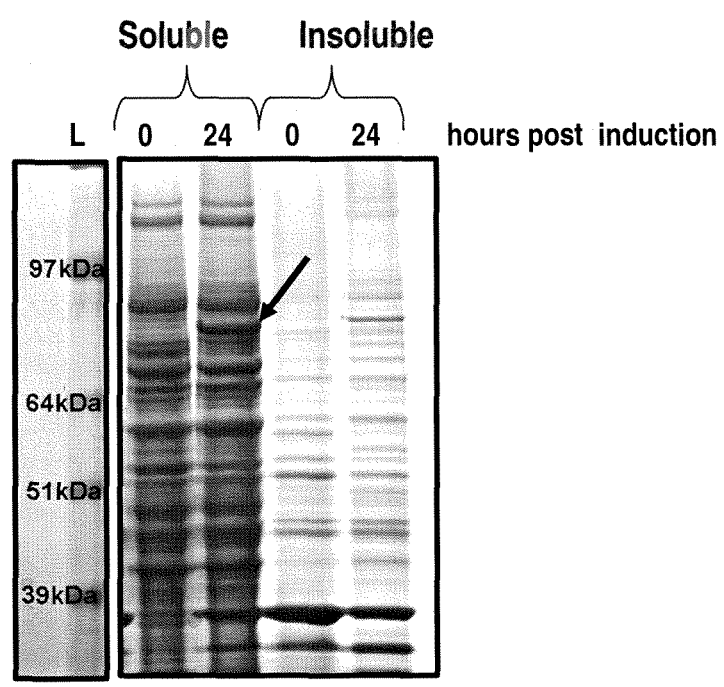
FIG. 4 illustrates expression of rPA83His without the native signal in the cytoplasm of *P. fluorescens*.
Figure 5:
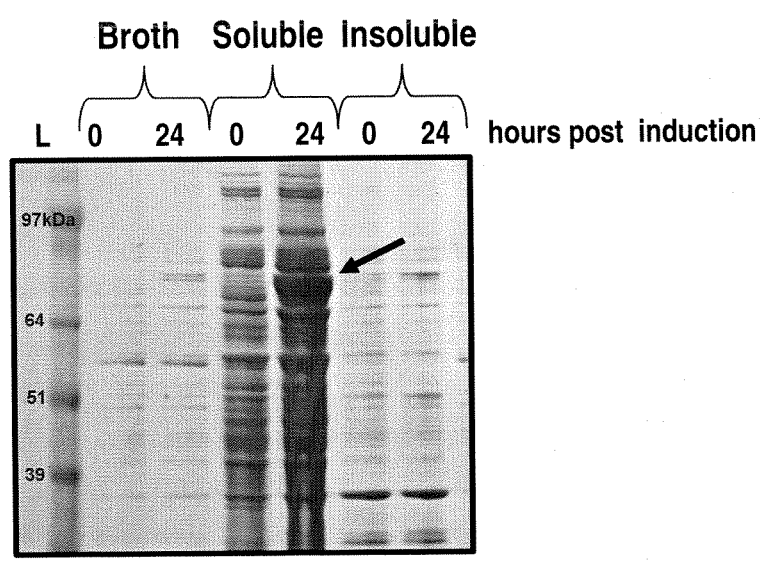
FIG. 5 illustrates expression of rPA83His with the pbp signal in the periplasm of *P. fluorescens*.
Figure 6:
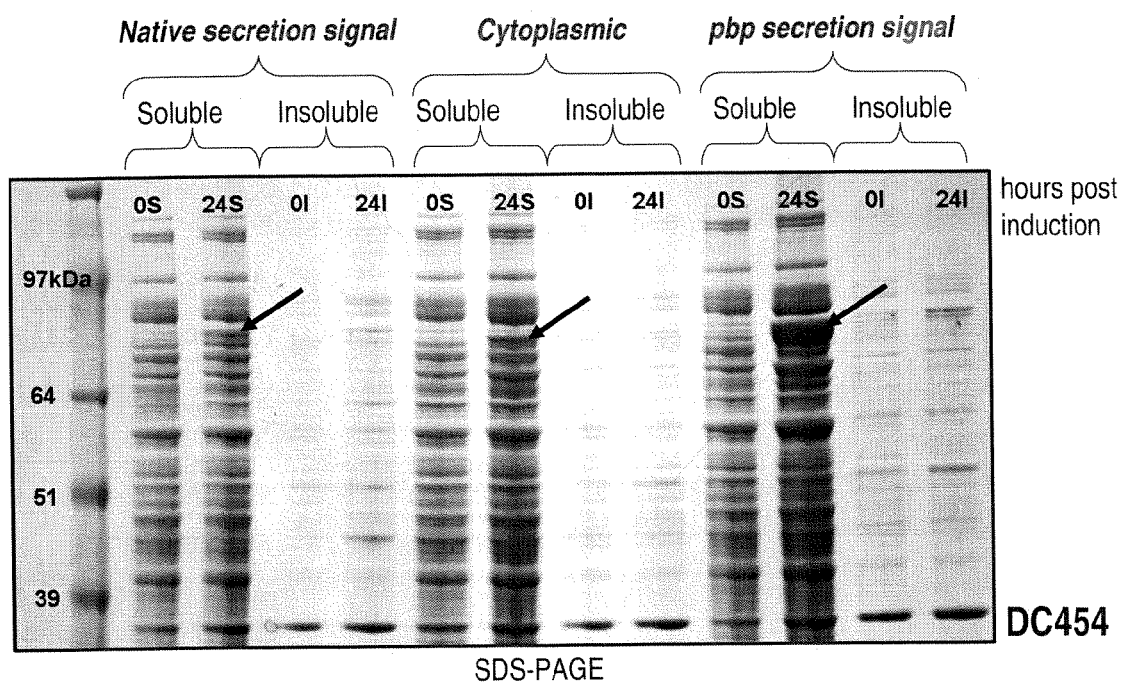
FIG. 6 illustrates expression of rPA83 without the His tag and with the native signal, without a signal and with the pbp signal in soluble and insoluble fractions of *P. fluorescens* DC454.
Figure 7:
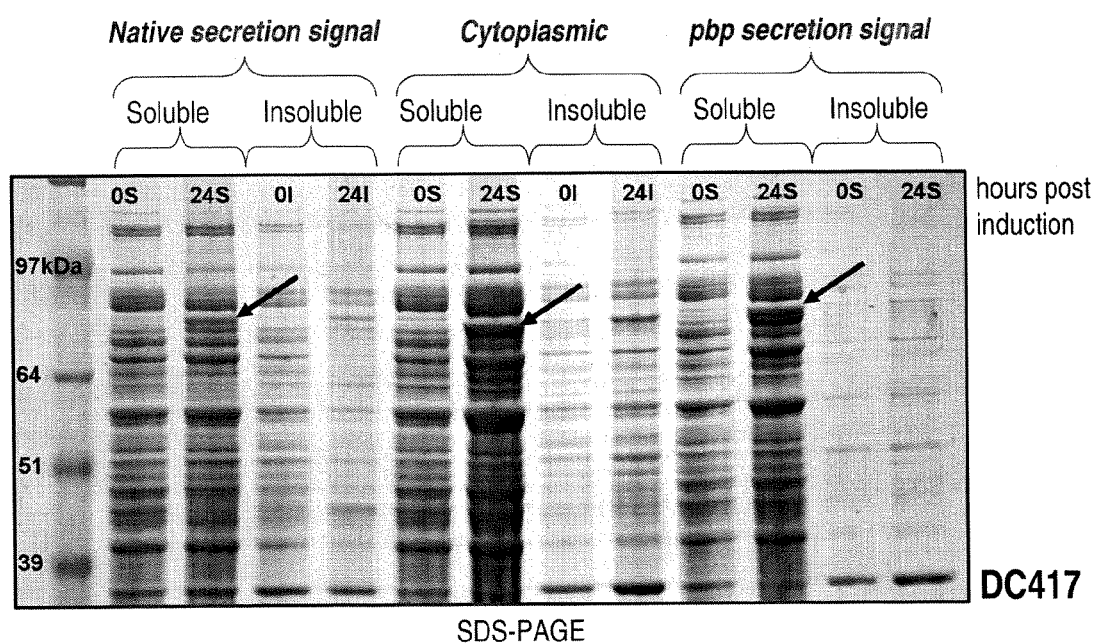
FIG. 7 illustrates expression of rPA83 without the His tag and with the native signal, without a signal and with the pbp signal in soluble and insoluble fractions of *P. fluorescens* DC417.
Figure 8:
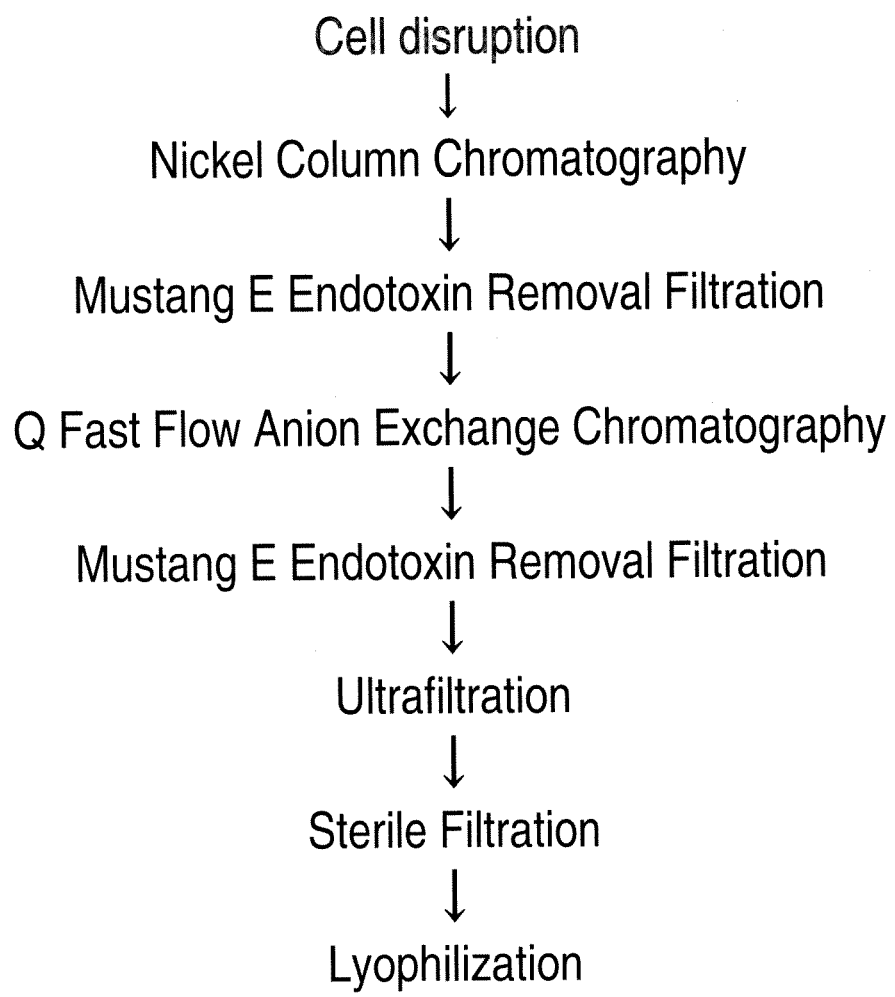
FIG. 8 illustrates purification scheme of heterologously expressed rPA83 with C-terminal His tag (PA83His)
Figure 9:
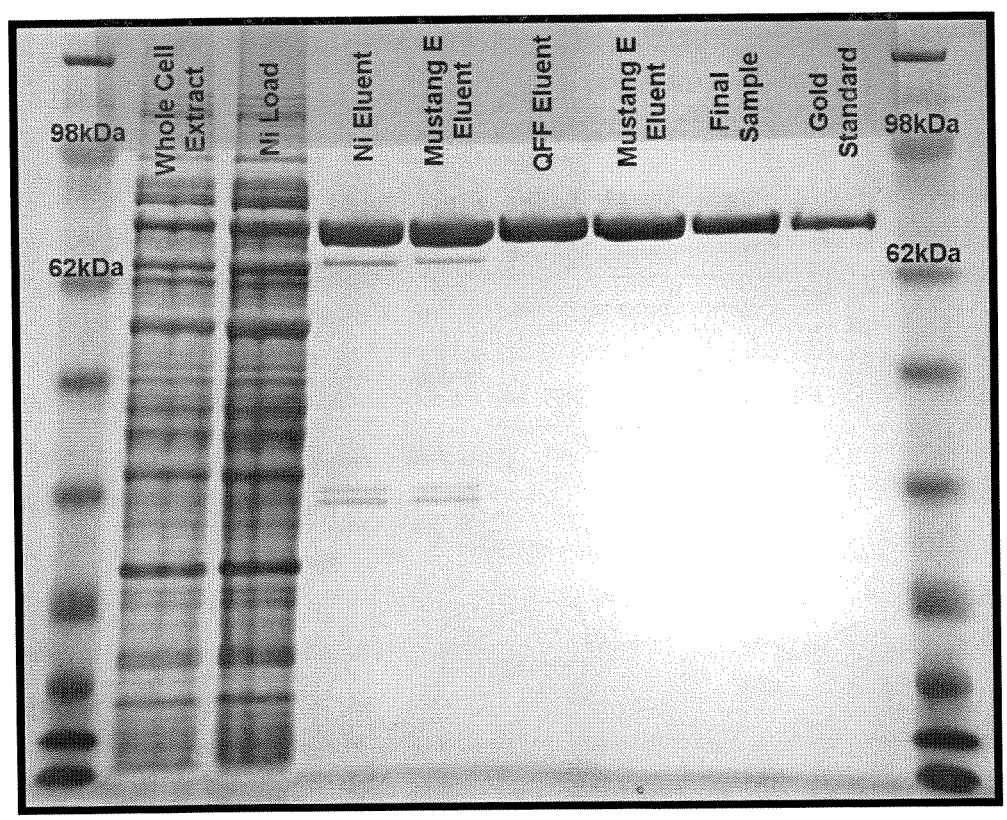
FIG. 9 illustrates steps in the purification of heterologously expressed rPA83 and final rPA83 sample as shown by 4-12% SDS-PAGE gel.
Figure 10:
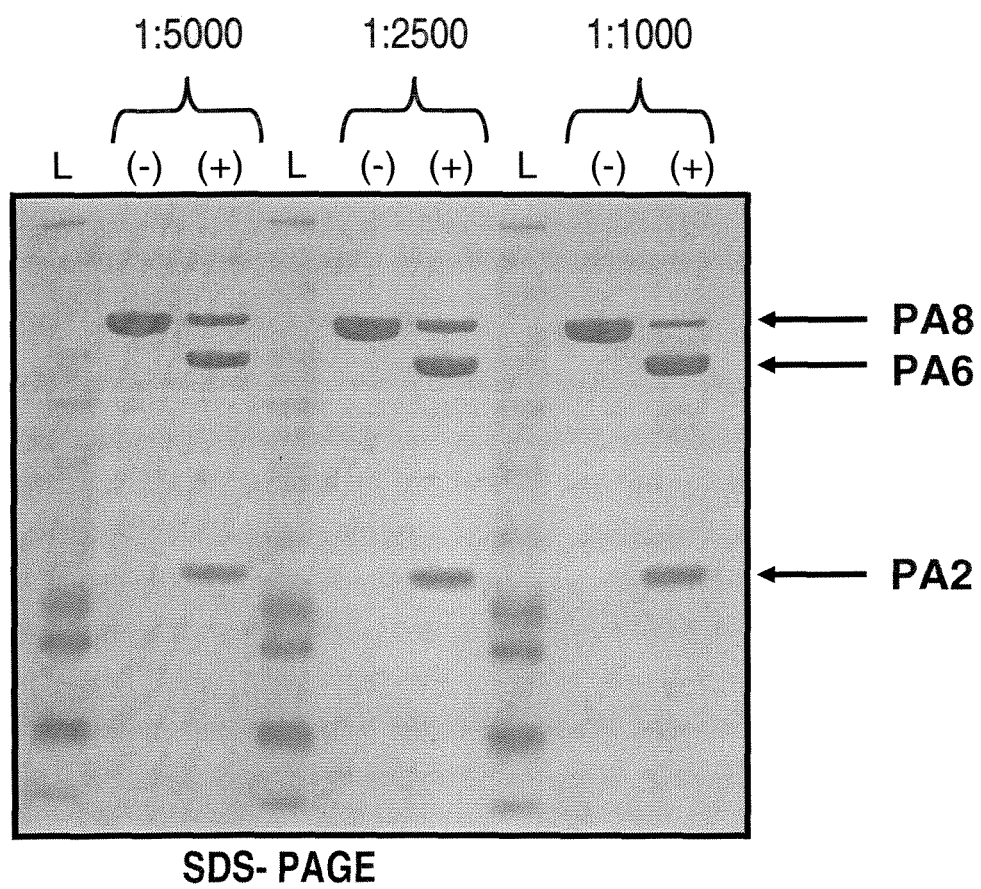
FIG. 10 illustrates cleavage of purified heterologously expressed rPA83 into PA63 and PA20 by trypsin as shown by 4-12% SDS-PAGE gel.

As illustrated by FIG. 2, the optimization process can begin by identifying the desired amino acid sequence to be heterologously expressed by the host. From the amino acid sequence a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures. Before the candidate DNA sequence is synthesized, the optimized sequence design can be checked to verify that the sequence correctly encodes the desired amino acid sequence. Finally, the candidate DNA sequence can be synthesized using DNA synthesis techniques, such as those known in the art.

In another embodiment of the invention, the general codon usage in a host organism, such as *P. fluorescens*, can be utilized to optimize the expression of the heterologous polynucleotide sequence. The percentage and distribution of codons that rarely would be considered as preferred for a particular amino acid in the host expression system can be evaluated. Values of 5% and 10% usage can be used as cutoff values for the determination of rare codons. For example, the codons listed in TABLE 1 have a calculated occurrence of less than 5% in the *P. fluorescens* MB214 genome and would be generally avoided in an optimized gene expressed in a *P. fluorescens* host.

TABLE 1

| Amino Acid(s) | Codon(s) Used | % Occurrence |
|---|---|---|
| G Gly | GGA | 3.26 |
| I Ile | ATA | 3.05 |
| L Leu | CTA | 1.78 |
|  | CTT | 4.57 |
|  | TTA | 1.89 |
| R Arg | AGA | 1.39 |
|  | AGG | 2.72 |
|  | CGA | 4.99 |
| S Ser | TCT | 4.18 |

A variety of host cells can be used for expression of a desired heterologous gene product. The host cell can be selected from an appropriate population of *E. coli* cells or *Pseudomonas* cells. Pseudomonads and closely related bacteria, as used herein, is co-extensive with the group defined herein as "Gram(−) Proteobacteria Subgroup 1." "Gram(−) Proteobacteria Subgroup 1" is more specifically defined as the group of Proteobacteria belonging to the families and/or genera described as falling within that taxonomic "Part" named "Gram-Negative Aerobic Rods and Cocci" by R. E. Buchanan and N. E. Gibbons (eds.), *Bergey's Manual of Determinative Bacteriology*, pp. 217-289 (8th ed., 1974) (The Williams & Wilkins Co., Baltimore, Md., USA) (hereinafter "Bergey (1974)"). The host cell can be selected from Gram-negative Proteobacteria Subgroup 18, which is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *P. fluorescens* biotype A, also called biovar 1 or biovar I (ATCC 13525); *P. fluorescens* biotype B, also called biovar 2 or biovar II (ATCC 17816); *P. fluorescens* biotype C, also called biovar 3 or biovar III (ATCC 17400); *P. fluorescens* biotype F, also called biovar 4 or biovar IV (ATCC 12983); *P. fluorescens* biotype G, also called biovar 5 or biovar V (ATCC 17518); *P. fluorescens* biovar VI; *P. fluorescens* Pf0-1; *P. fluorescens* Pf-5 (ATCC BAA-477); *P. fluorescens* SBW25; and *P. fluorescens* subsp. *cellulosa* (NCIMB 10462).

The host cell can be selected from Gram-negative Proteobacteria Subgroup 19, which is defined as the group of all strains of *P. fluorescens* biotype A, including *P. fluorescens* strain MB101, and derivatives thereof.

In one embodiment, the host cell can be any of the Proteobacteria of the order Pseudomonadales. In a particular embodiment, the host cell can be any of the Proteobacteria of the family Pseudomonadaceae. In a particular embodiment, the host cell can be selected from one or more of the following: Gram-negative Proteobacteria Subgroup 1, 2, 3, 5, 7, 12, 15, 17, 18 or 19.

Additional *P. fluorescens* strains that can be used in the present invention include *P. fluorescens* Migula and *P. fluorescens* Loitokitok, having the following ATCC designations: [NCIB 8286]; NRRL B-1244; NCIB 8865 strain COI; NCIB 8866 strain CO2; 1291 [ATCC 17458; IFO 15837; NCIB 8917; LA; NRRL B-1 864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [IEM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108[52-22; IFO 15832]; 143 [IFO 15836; PL]; 149 [2-40-40; IFO 15838]; 182 [IFO 3081; PJ 73]; 184 [IFO 15830]; 185[W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198[PJ 302]; 201 [PJ 368]; 202 [PJ 372]; 203 [PJ 376]; 204 [IFO 15835; PJ 682]; 205[PJ686]; 206 [PJ 692]; 207 [PJ 693]; 208 [PJ 722]; 212 [PJ 832]; 215 [PJ 849]; 216 [PJ885]; 267 [B-9]; 271 [B-1612]; 401 [C71A; IFO 15831; PJ 187]; NRRL B-3178 [4; IFO 15841]; KY8521; 3081; 30-21; [IFO 3081]; N; PYR; PW; D946-B83 [BU 2183; FERM-P 3328]; P-2563 [FERM-P 2894; IFO 13658]; IAM-1126 [43F]; M-1; A506 [A5-06]; A505[A5-05-1]; A526 [A5-26]; B69; 72; NRRL B4290; PMW6 [NCIB 11615]; SC 12936; A1 [IFO 15839]; F 1847 [CDC-EB]; F 1848 [CDC 93]; NCIB 10586; P17; F-12; AmMS 257; PRA25; 6133D02; 6519E01; Ni; SC15208; BNL-WVC; NCTC 2583 [NCIB 8194]; H13; 1013 [ATCC 11251; CCEB 295]; IFO 3903; 1062; or Pf-5.

Transformation of the *Pseudomonas* host cells with the vector(s) may be performed using any transformation methodology known in the art, and the bacterial host cells may be transformed as intact cells or as protoplasts (i.e. including cytoplasts). Transformation methodologies include poration methodologies, e.g., electroporation, protoplast fusion, bacterial conjugation, and divalent cation treatment, e.g., calcium chloride treatment or CaCl/Mg$^{2+}$treatment, or other well known methods in the art. See, e.g., Morrison, *J. Bact.*, 132:349-351 (1977); Clark-Curtiss & Curtiss, Methods in Enzymology, 101:347-362 (Wu et al., eds, 1983), Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

As used herein, the term "fermentation" includes both embodiments in which literal fermentation is employed and embodiments in which other, non-fermentative culture modes are employed. Fermentation may be performed at any scale. In embodiments of the present invention the fermentation medium can be selected from among rich media, minimal media, and mineral salts media; a rich medium can also be used. In another embodiment either a minimal medium or a mineral salts medium is selected. In still another embodiment, a minimal medium is selected. In yet another embodiment, a mineral salts medium is selected. Mineral salts media are generally used.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli (1950) in *J. Bact.* 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium can contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

In one embodiment, media can be prepared using the various components listed below. The components can be added in the following order: first $(NH_4)HPO_4$, $KH_2PO_4$ and citric acid can be dissolved in approximately 30 liters of distilled water; then a solution of trace elements can be added, followed by the addition of an antifoam agent, such as Ucolub N 115. Then, after heat sterilization (such as at approximately 121. degree. C.), sterile solutions of glucose $MgSO_4$ and thiamine-HCL can be added. Control of pH at approximately 6.8 can be achieved using aqueous ammonia. Sterile distilled water can then be added to adjust the initial volume to 371 minus the glycerol stock (123 mL). The chemicals are commercially available from various suppliers, such as Merck. This media can allow for a high cell density cultivation (HCDC) for growth of *Pseudomonas* species and related bacteria. The HCDC can start as a batch process which is followed by a two-phase fed-batch cultivation. After unlimited growth in the batch part, growth can be controlled at a reduced specific growth rate over a period of 3 doubling times in which the biomass concentration can increased several fold. Further details of such cultivation procedures is described by Riesenberg, D.; Schulz, V.; Knorre, W. A.; Pohl, H. D.; Korz, D.; Sanders, E. A.; Ross, A.; Deckwer, W. D. (1991) "High cell density cultivation of. *Escherichia coli*, at controlled specific growth rate" J Biotechnol: 20(1) 17-27. TABLE-US-00005 TABLE 5 Medium composition Component Initial concentration $KH_2PO_4$ 13.3 gl$^{-1}$ $(NH_4)_2HPO_4$ 4.0 g l$^{-1}$ Citric acid 1.7 g l$^{-1}$ $MgSO_4$-$7H_2O$ 1.2 g l$^{-1}$ Trace metal solution 10 mll$^{-1}$ Thiamin HCl 4.5 mg l$^{-1}$ Glucose-$H_2O$ 27.3 g l$^{-1}$ Antifoam Ucolub N115 0.1 ml l$^{-1}$ Feeding solution $MgSO_4$-$7H_2O$ 19.7 g l$^{-1}$ Glucose-$H_2O$ 770 g l$^{-1}$ $NH_3$ 23 g Trace metal solution 6 g l$^{-1}$ Fe (111) citrate 1.5 g l$^{-1}$ $MnCl_2$-$4H_2O$ 0.8 g l$^{-1}$ $ZmCH_2COOl_2$-$2H_2O$ 0.3 g l$^{-1}$ $H_3BO_3$ 0.25 g l$^{-1}$ $Na_2MoO_4$-$2H_2O$ 0.25 g l$^{-1}$ $CoCl_2$ $6H_2O$ 0.15 g l$^{-1}$ $CuCl_2$ $2H_2O$ 0.84 g l$^{-1}$ ethylene diaminetetracetic acid $Na_2$ salt $2H_2O$ (Titriplex III, Merck).

The protective antigen precursor PA83 of *Bacillus anthracis*, strain Sterne (764 aa) has previously been submitted under NCBI Accession Number AAA22637 and contains the following amino acid sequence: mkkrkvlipl malstilvss tgnleviqae vkqenrllne sesssqgllg yyfsdlnfqa pmvvtssttg dlsipssele nipsenqyfq saiwsgfikv kksdeytfat sadnhvtmwv ddqevinkas nsnkirlekg rlyqikiqyq renptekgld fklywtdsqn kkevissdnl qlpelkqkss nsrkkrstsa gptvpdrdnd gipdsleveg ytvdvknkrt flspwisnih ekkgltkyks spekwstasd pysdfekvtg ridknvspea rhplvaaypi vhvdmeniil sknedqstqn tdsetrtisk ntstsrthts evhgnaevha sffdiggsys agfsnsnsst vaidhslsla gertwaetmg lntadtarin aniryvntgt apiynvlptt slvlgknqt1 atikakenql sqilapnnyy psknlapial naqddfsstp itmnynqfle lektkqlrld tdqvygniat ynfengrvry dtgsnwsevl pqiqettari ifngkdlnlv erriaavnps dplettkpdm tlkealkiaf gfnepngnlq yqgkditefd fnfdqqtsqn iknqlaelna tniytvldki klnakmnili rdklplydrn niavgadesv vkeahrevin ssteglllni dkdirkilsg yiveiedteg lkevindryd mlnisslrqd gktfidkky ndklplyisn pnykvnvyav tkentiinps engdtstngi kkilifskkg yeig (SEQ ID NO: 1) (SEQ ID NO:19 is the native signal peptide, including initial methionine, shown in bold; SEQ ID NO:20 is the PA83 protein sequence shown in plain text). Met has been added for translation start and the native signal was removed when protein was expressed in *P. fluorescens* without the signal peptide. This sequence has been codon optimized for expression utilizing the elements discussed above. SEQ ID NOs: 2 and 10-15 illustrate optimized nucleotide sequences.

When the recombinant molecule takes the form of an expression system, the transformed or transfected cells can be used as a source of the protein or polypeptide specified as amino acid sequence in SEQ ID NO: 1, TPA-PA, MAT-PA, and PA63.

The sequences recited in this application may be homologous (have similar identity). Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, 96%, 97%, 98% or 99% or more can also be used to establish homology. Methods for determining sequence similarity percentages (e.g., BLASTP and BLASTN using default parameters) are described herein and are generally available.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345 358; Hein J. (1990) Unified Approach to Alignment and Phylogenes pp. 626 645 Methods in Enzymology vol. 183, Academic Press, Inc., San Diego, Calif.; Higgins, D. G. and Sharp, P. M. (1989) CABIOS 5:151 153; Myers, E. W. and Muller W. (1988) CABIOS 4:11 17; Robinson, E. D. (1971) Comb. Theor 11:105; Santou, N. Nes, M. (1987) Mol. Biol. Evol. 4:406 425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) *Proc. Natl. Acad., Sci.* USA 80:726 730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that can be suitable for determining percent sequence identity and sequence similarity are the BLAST and BLAST 2.0 algorithms, which are described in Altschul et al. (1977) *Nucl. Acids Res.* 25:3389 3402 and Altschul et al. (1990) *J. Mol. Biol.* 215:403 410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, nucleic acid sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46, 1985; Murphy et al., *Proc. Natl. Acad. Sci.* USA 83:8258 8262, 1986; U.S. Pat. No. 4,935,233 and U.S. Pat. No. 4,751, 180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

In another embodiment, the present-invention relates to an anthrax vaccine comprising one or more of the codon optimized sequences encoding one or more B. anthracis proteins or polypeptides as described throughout. The present invention relates a method for providing immunity against anthrax said method comprising administering one or more of the codon optimized sequences encoding for any combination of the B. anthracis proteins to a subject such that a protective immune reaction is generated.

Administration of the proteins disclosed herein may be carried out by any suitable means, including both parenteral injection (such as intraperitoneal, subcutaneous, or intramuscular injection), or topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the protein as an aerosol suspension, and then causing the subject to inhale the respirable particles. Methods and apparatus for administering respirable particles of pharmaceutical formulations are well known, and any conventional technique can be employed. An "immunogenic amount" is an amount of the protein sufficient to evoke an immune response in the subject to which the vaccine is administered.

When the nucleic acids are used as a vaccine, the nucleic acids can be administered directly using techniques such as delivery on gold beads (gene gun), delivery by liposomes, or direct injection, among other methods known to people in the art. Any one or more constructs or replicating a nucleic acid can be used in any combination effective to elicit an immunogenic response in a subject. Generally, the nucleic acid vaccine administered may be in an amount of about 1-5 ug of nucleic acid per dose and will depend on the subject to be treated, capacity of the subject's immune system to develop the desired immune response, and the degree of protection desired. Precise amounts of the vaccine to be administered may depend on the judgment of the practitioner and may be peculiar to each subject and antigen.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

The present invention is explained in greater detail in the Examples that follow. These examples are intended as illustrative of the invention and are not to be taken are limiting thereof.

EXAMPLES

Example 1

Expression and Purification of rPA from P. fluorescens

P. fluorescens has been used to express rPA vaccine antigen rPA83 (SEQ ID NO: 1), rPA63, and rPA-D4 (FIG. 1). Codon optimized polynucleotide sequences that contained SpeI and XhoI flanking restriction sites were synthesized. There are a number of alternative sequences for the codon optimized polynucleotide sequence for expression in P. fluorescence that encode the desired rPA including, rPA83His with the native signal and C-terminal His tag (SEQ ID NO: 2), rPA83 with the native signal peptide (SEQ ID NO: 10), rPA83 without the native signal peptide (SEQ ID NO: 11), rPA83 with an N-terminal phosphate binding protein (php) secretion signal (SEQ ID NO: 12), rPA83 with C-terminal His tag and without the native signal peptide (SEQ ID NO: 13), rPA63His with C-terminal His tag (SEQ ID NO: 14), and DrPAd4His Domain 4 with C-terminal His tag. Further examples of alternative polynucleotide sequences encoding for codon optimized rPA83 include the polynucleotide sequences as shown in SEQ ID NOs: 16-18.

To direct the expression into the cytoplasm, the genes were amplified from their corresponding plasmids by PCR, during which the native secretion signal was removed and AUG codon was incorporated to provide the translation start site (i.e., SEQ IDs NO: 11 and 13). To direct the expression into the periplasm, the genes were amplified from their corresponding plasmids by PCR, during which the periplasmic secretion signal derived from the pbp was fused to the coding sequences for the mature protein (i.e., SEQ ID NO:12). PCR products were subcloned into the shuttle plasmid and verified by sequencing. Upon verification, the genes were cloned into the P. fluorescens expression vector containing the tac promoter and pyrF selection marker, and transformed by electroporation into the P. fluorescens DC454 (ΔpyrF lsc::lacIQ1) or DC417 (ΔhslUV::ΔpyrF lsc::lacIQ1) strains. The colonies that grew on the M9+1% Glucose media in the absence of uracil were screened by restriction digest for the presence of inserts. Cells from selected colonies were grown in media at shake-flask scale and induced with IPTG. OD $A_{600}$ readings were taken at various times during fermentation to monitor cell growth. Cells were collected at 24 hrs post induction, and both soluble and insoluble fractions were analyzed by SDS-PAGE gel. PBS buffer, pH 7.4.

When using the native PA leader sequence (i.e., SEQ ID NO:2), the heterologous expression resulted in most of the protein being present in the culture media, which can simplify the purification of the heterologous protein.

Example 2

Cloning and Expression of 83 kDa rPA83His with Native Signal in DC454

Cloning: An rPA insert was excised out of plasmid pJ3: G01196 (DNA 2.0) with SpeI and XhoI. The insert was gel purified on 1% agarose gel and ligated into vector pDow1169, (a medium copy plasmid with RSF1010 origin, pyrF, a ribosome binding site under control of the tac promoter and the rrnBT1T2 terminator from pKK223-3 (PL-Pharmacia)), which had been digested with SpeI, XhoI and treated with Alkaline Phosphatase. The ligation product was transformed by electroporation into *P. fluorescens* DC454 strain after purification with Micro Bio-spin 6 Chromatography columns. The transformants were plated on M9 Glucose plate after shaking for two hours in LB media at 30° C. The presence of the insert was confirmed by restriction digest and sequencing.

Protein Expression: Single transformants were inoculated into 50 ml M9 Glucose media and grown overnight. *P. fluorescens* cultures of 3.0-5.0 OD600 were used to inoculate the shake-flask media. Shake flasks were incubated at 30° C with 300 rpm shaking overnight. Overnight cultures of 15.0-20.0 OD600 were induced with 300 µM isopropyl-β-D-thiogalactopyranoside (IPTG). Cultures were harvested at 24 hours post induction. When using the native PA leader sequence (i.e., SEQ ID NO: 2), the heterologous expression resulted in the protein being unexpectedly present in the culture media, which simplifies the purification of the heterologous rPA83 protein (FIG. 3).

Example 3

Cloning and Expression of 83 kDa rPA83His Without Native Signal in *P. fluorescens* DC454

Cloning: The insert was amplified by PCR with forward primer PA-nosig-SpeI-F 5'-CTACTAGTAGGAGGTAACTTATGGAAGTGAAGCAGGAGAATCG-3' (SEQ ID NO: 3) and reverse primer PA-Xho-Rev 5'-CCGCTCGAGTCATTAATGATGGTGGTGATGGTGCCCGATCTC-3' (SEQ ID NO: 4) with the plasmid pJ3:G01196 as the template. The insert was amplified with the PCR protocol of TABLE 2. The PCR product was purified with Qiaquick PCR purification kit (Qiagen), digested with SpeI and XhoI (NEB) and purified again with Qiaquick kit before ligating into the expression vector with T4 DNA ligase. The ligation product was transformed by electroporation into *P. fluorescens* strain DC454 after purification with Micro Bio-spin 6 Chromatography columns. The transformants were plated on M9 Glucose plate after two hours shaking in LB media at 30° C. The plates were incubated at 30° C. for 48 hours. The presence of the insert was confirmed by restriction digest and sequencing.

TABLE 2

PCR PROTOCOL

| Reaction Mix (100 μL total volume) | Thermocycling Steps | | | |
|---|---|---|---|---|
| 10 μL 10× Pt HiFi buffer * | Step 1 | 1 Cycle | 2 min. | 94° C. |
| 4 μL 50 mM $MgSO_4$ * | Step 2 | 35 Cycles | 30 sec. | 94° C. |
| 2 μL 10 mM dNTPs * | | | 30 sec. | 55° C. |
| 0.25 mg Each Primer | | | 3 min. | 68° C. |
| 1-5 ng Template DNA | Step 3 | 1 Cycle | 10 min. | 70° C. |
| 1 μL Pt HiFi Taq DNA Polymerase * | Step 4 | 1 Cycle | Maintain | 4° C. |
| Remainder Distilled De-ionized $H_2O$ ($ddH_2O$) | | | | |

(* from Invitrogen Corp, Carlsbad, CA, USA, hereinafter "Invitrogen")

Protein Expression: Single transformants were inoculated into 50 ml M9 Glucose media and grown overnight. *P. fluorescens* cultures of 3.0-5.0 OD600 were used to inoculate shake-flask media. Shake flasks were incubated at 30° C. with 300 rpm shaking overnight. Overnight cultures of 15.0-20.0 OD600 were induced with 300 μM isopropyl-β-D-thiogalactopyranoside (IPTG). Cultures were harvested at 24 hours post induction. High levels of expression of soluble rPA83 (SEQ ID NO: 13), were detected in the cytoplasmic fractions. The rPA83 was purified from the cell lysate using multiple chromatography steps. The procedure was designed to minimize degradation of the PA protein during purification. The purification scheme is illustrated in FIG. 8 and described in details in Example 8. Purification results are shown in FIGS. 9-10. The purified protein was stored in 5 mM Hepes, 50 mM NaCl, at pH 7.5 at −80° C. or was lyophilized and stored at 4° C. The yields of purified protein were 1.03 g/L. The majority of the expressed protein was expressed in the soluble fraction. (FIG. 4). The arrow illustrates rPA83 with no signal sequence. The expression of soluble PA protein in the cytoplasm of *P. fluorescens* can eliminate the need for refolding that was previously used for insoluble rPA83 expressed in the cytoplasm of *E. coli*.

Example 4

Cloning and Expression of 63 kDa rPA63His in DC454

Cloning: The nucleic acid sequence coding the C-term 63 kDa portion of the 83 kDa rPA was amplified out of plasmid pJ3:G01196 (DNA 2.0) with the following PCR primers: A63-For 5'-CTACTAGTAGGAGGTAACTTATGTCGACCTCCGCTGG GCCTACGG-3' (SEQ ID NO: 5) and PA-Xho-Rev (SEQ ID NO:4), following the PCR protocol shown in TABLE 2.

The PCR product was purified with Qiaquick PCR purification kit (Qiagen), digested with SpeI and XhoI (NEB), and purified again with Qiaquick kit before ligating into an expression vector with T4 DNA ligase. The ligation product was transformed by electroporation into *P. fluorescens* strain DC454 after purification with Micro Bio-spin 6 Chromatography columns. The transformants were plated on M9 Glucose plate after two hours of shaking in LB media at 30° C. The plates were incubated at 30° C. for 48 hours. The presence of the insert was confirmed by restriction digest and sequencing.

Protein Expression: Single transformants were inoculated into 50 ml M9 Glucose media and grown overnight. *P. fluorescens* cultures of 3.0-5.0 OD600 were used to inoculate to the shake-flask media. Shake flasks were incubated at 30° C. with 300 rpm shaking overnight. Overnight cultures of 15.0-20.0 OD600 were induced with 300 μM isopropyl-β-D-thiogalactopyranoside (IPTG). Cultures were harvested at 24 hours post induction.

Example 5

Cloning and Expression of rPAd4His Domain 4 in DC454

Cloning: The nucleic acid sequence coding the C-term domain 4 portion of the 83 kDa rPA was amplified out of plasmid pJ3:G01196 with the following primers: PAdomain4-SpeI-For 5'-CTACTAGTAGGAGGTAACTTATGGAGCTGAACGCCACCAAC-3' (SEQ ID NO: 6) and PA-Xho-Rev (SEQ ID NO: 4).

The PCR protocol and the protein expression was the same as those previously described. The cultures were harvested at 24 hours post induction.

Example 6

Cloning and Expression of 83 kDa rPA83His in the periplasm of DC454

Cloning: A 24 residue phosphate binding protein (pbp) secretion signal was fused to the N-terminus of 83 kDa rPA protein without its native secretion signal and the starting Methionine, Pbp signal was amplified out of pDOW1113 with the following primer pair: pbpF-SpeI 5'-GGACTAG-TAGGAGGTAACTTATGAAACTGAAACGTTTGATG-3' (SEQ ID NO: 7) and pbp-PA-Rev 5'-CAGAACCTTGCGCT-TCTTGGCCACCGCGTTGGC-3' (SEQ ID NO: 8).

83 kDa rPA was amplified by PCR with the following primer pair: pbp-PA-For 5'-GCCAAGCGCGGTGGCCAA-GAAGCGCAAGGTTCTG-3' (SEQ ID NO: 9) and PA-Xho-Rev (SEQ ID NO: 4). The two PCR products were combined in a Splicing by Overlapping Extension PCR (SOE-PCR) using the following primer pair: pbpF-SpeI (SEQ ID NO: 7) and PA-Xho-Rev (SEQ ID NO: 4). The PCR protocol, subcloning procedure, and protein expression were performed in the same manner as those previously described. The cultures were harvested at 24 hours post induction. Unexpectedly high levels of expression of soluble rPA83, were detected in the soluble fractions (FIG. 5).

Example 7

Cloning and expression of 83 kDa rPA83 Without the His tag in the Cytoplasm and Periplasm of DC454 and DC417

The cloning, PCR protocol, subcloning procedure, and protein expression were performed in the same manner as those previously described. The cultures were harvested at 24 hours post induction. Unexpectedly high levels of expression of soluble rPA83 with the native signal (SEQ ID NO: 10), rPA83 without the native signal (SEQ ID NO: 11) and rPA83 with the pbp signal (SEQ ID NO: 12) were detected in the soluble fractions (FIG. 6 and 7).

Example 8

Purification

Purification and analysis of rPA83His: The purification scheme and results are shown in FIGS. 8-10. It was important to work quickly, keep samples at 4° C. and perform the purification without stopping between individual steps to prevent unwanted degradation of rPA83 during purification. The designed protocol described bellow resulted in purification of high quality rPA83 as shown by single band on an SDS-PAGE gel (FIG. 9).

French Press: The lysis buffer consisted of 20 mM Tris, 10 mM Imidizol, 300 mM NaCl at pH 8.0. PMSF was added to the lysis buffer to final concentration of 10 mM. 8 grams of *P. fluorescens* rPA83His cell pellet was suspended in 40 ml of lysis buffer with PMSF. Addition of PMSF was important to prevent unwanted degradation of rPA83 during purification. The cells were passed through the French press two times at a pressure of 1,280 pounds per square inch. The samples were spun at 10,000 G for 30 minutes to remove the insoluble fraction.

The following purification steps were the provided. First Nickel Chromatography was used. The supernatant was filtered through a 0.45 um glass fiber filter prior to loading onto the nickel column. The sample was loaded onto a 15 ml nickel charged His-Bind resin from Novagen at 37 cm/hr. Nickel binding/wash buffer A was 20 mM Tris, 10 mM Imidizol, 300 mM NaCl, at pH 8.0. Nickel elution buffer B was 20 mM Tris, 1.0M Imidizol, 300 mM NaCl, pH 8.0. The column was washed with 4 column volumes of nickel binding/wash buffer A. Then, the column was washed with 5 column volumes of 1% nickel elution buffer B. The rPA83His was eluted with an 8 column volume gradient from 1% nickel elution buffer B to 20% nickel elution buffer B at 15 cm/hr.

Next Mustang E endotoxin filtration was utilized. The rPA83His eluent from the nickel column was passed through a Mustang E endotoxin filter at 2 ml/minute. Afterwards, 10 KDa Ultrafiltration was performed. The Mustang E filtrate was buffer exchanged 2 times with a 15 ml 10 kDa ultracentrifugation spin column into anion exchange wash buffer A, which was composed of 20 mM Hepes at pH 7.0.

Then a superose Q Fast Flow Anion Exchange (QFF column) was utilized. The sample was loaded onto a prepacked 5 ml superose Q fast flow column at 5 ml/minute. The column was washed with 10 column volumes of 7.5% anion exchange elution buffer B, which consisted of 20 mM Hepes, 1.0M NaCl, at pH 7.0. The rPA83His was eluted with a 20 column volume gradient from 7.5% anion exchange elution buffer B to 50% anion exchange elution buffer B.

The next step of purification involved a Mustang E Endotoxin Filtration. The rPA83His eluent from the QFF column was passed through a Mustang E endotoxin filter at 2 ml/minute. Then under 10 KDa ultrafiltration, the Mustang E filtrate was buffer exchanged 2 times with a 15 ml 10 kDa ultracentrifugation spin column into final buffer, which was composed of 5 mM Hepes, 50 mM NaCl, at pH 7.5. The final sample was sterile filtered using 0.22 μm filter. The samples were then frozen at −20° C., lyophilized overnight, and vacuum sealed the next day.

SDS-PAGE: The whole cell extract, nickel column load, nickel column eluent, the Mustang E elutent, the QFF eluent, second Mustang E eluent, final sample, and *Bacillus anthracis* PA (Gold Standard) were run on a 4-12% SDS-PAGE gel (FIG. 9). The gel was stained with simply blue safe stain from Invitrogen. A single band of 83 kDa was detected in the final sample.

Trypsin Cleavage: 1 mg/ml rPA83His was incubated with 1:5000, 1:2500, and 1:1000 w/w ratio of trypsin to rPA83His in 25 mM Hepes, 1 mM CaCl2, and 50 mM NaCl, at pH 8.50 for 35 minutes at RT. The reaction was stopped by adding the SDS-PAGE loading buffer and the samples are immediately run on a 4-12% SDS-PAGE gel (FIG. 10) The purified rPA83 cleaved into PA63 and PA20 as expected.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method of producing a soluble recombinant *Bacillus anthracis* protective antigen protein (rPA) in a *Pseudomonas fluorescens* expression system comprising expressing the soluble rPA from a nucleotide sequence encoding the soluble rPA, wherein the nucleotide sequence is the soluble rPA encoding sequence of a nucleotide sequence selected from the group consisting of SEQ ID NO:2, SEQ ID NO:10, SEQ ID NO:11, SEQ ID NO:12, SEQ ID NO:13, and SEQ ID NO:14, or wherein the nucleotide sequence encoding the soluble rPA is a nucleotide sequence which is at least 95% identical to the nucleotide sequence of SEQ ID NO:2, SEQ ID NO:10, SEQ ID NO:11, SEQ ID NO:12, SEQ ID NO:13, or SEQ ID NO:14.

2. The method of claim 1, wherein the soluble rPA encoding nucleotide sequence lacks the sequence encoding the starting methionine.

3. The method of claim 1, wherein the soluble rPA is expressed in the cytoplasm or periplasm of a host cell.

4. The method according to claim 1, comprising expressing the soluble rPA to which a secretion signal has been fused, wherein said secretion signal co-translationally or post-translationally directs transfer of the soluble rPA to the periplasm of a host cell.

* * * * *

SEQUENCE LISTING

<160> NUMBER OF SEQ ID NOS: 20

<210> SEQ ID NO 1

```
<211> LENGTH: 764
<212> TYPE: PRT
<213> ORGANISM: Bacillus anthracis

<400> SEQUENCE: 1

Met Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Glu Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400
```

```
Ala Pro Ile Tyr Asn Val Leu Pro Thr Thr Ser Leu Val Leu Gly Lys
            405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
            435                 440                 445

Ala Leu Asn Ala Gln Asp Asp Phe Ser Ser Thr Pro Ile Thr Met Asn
            450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
                500                 505                 510

Ile Gln Glu Thr Thr Ala Arg Ile Ile Phe Asn Gly Lys Asp Leu Asn
            515                 520                 525

Leu Val Glu Arg Arg Ile Ala Ala Val Asn Pro Ser Asp Pro Leu Glu
            530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
                580                 585                 590

Asn Gln Leu Ala Glu Leu Asn Ala Thr Asn Ile Tyr Thr Val Leu Asp
            595                 600                 605

Lys Ile Lys Leu Asn Ala Lys Met Asn Ile Leu Ile Arg Asp Lys Arg
            610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
                660                 665                 670

Val Glu Ile Glu Asp Thr Glu Gly Leu Lys Glu Val Ile Asn Asp Arg
                675                 680                 685

Tyr Asp Met Leu Asn Ile Ser Ser Leu Arg Gln Asp Gly Lys Thr Phe
            690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
                740                 745                 750

Ile Leu Ile Phe Ser Lys Lys Gly Tyr Glu Ile Gly
            755                 760
```

<210> SEQ ID NO 2
<211> LENGTH: 2313
<212> TYPE: DNA
<213> ORGANISM: Bacillus anthracis

<400> SEQUENCE: 2
atgaagaagc gcaaggttct gatcccattg atggccttgt cgaccatcct ggtgtcctcc    60

```
accggcaatt tggaagtgat ccaggctgaa gtgaagcagg agaatcgcct gctgaacgag        120
tcggagagct cgtcgcaggg cctcctgggc tactactttt cggatttgaa ctttcaggct        180
cccatggtgg tgaccagtag tacgaccggt gacctgtcca tcccgtccag cgaactggaa        240
aacattccgt cggaaaacca gtacttccaa agcgcgattt ggagcggctt catcaaggtc        300
aagaagtcgg acgaatacac ttttgccacc agcgctgaca accatgtgac catgtgggtg        360
gatgaccagg aagtcattaa caaggcctcc aacagcaaca aaatccgtct ggagaaaggt        420
cgcttgtatc agatcaaaat ccaataccaa cgcgaaaacc cgacggaaaa gggcttggac        480
ttcaagctgt actggaccga cagccaaaac aagaaggagg tcatctcctc cgacaacctg        540
cagctgcccg agctgaaaca gaagtcgtcg aattcgcgca gaaacggtc gacctccgct         600 gggcctacgt tgccagaccg cgacaacgac ggtatcccg actcgctgga agttgagggt         660
tatactgtgg atgtcaagaa caagcgtacc ttcctgagcc cctggatctc gaatatccat        720
gagaagaagg gtctcacgaa gtacaagtcc agtcccgaga atggagcac cgcgagcgac         780 ccgtactccg acttcgaaaa ggtcactggc cgtattgata gaacgtttc ccctgaagct         840 cggcatccgt tggttgcagc ctacccgatc gtgcatgttg acatggaaaa cattatcctg        900
agcaagaacg aagaccagag cacccagaat accgactccg aaacccgcac cattagcaag        960
aacacgtcca cgagccgcac ccatacctcg gaggtccacg gtaacgcgga agtgcacgcc       1020
tcgttcttcg atattggtgg gtcggtgtcc gctggtttca gcaactccaa ttcgagcacc       1080
gtcgccatcg accactcgct gtccttggct ggtgagcgca cctgggcaga gaccatgggg       1140
ctgaacaccg cagacaccgc acgtctgaac gcgaatatcc gctacgtgaa caccggcacc       1200
gcacccatct acaacgtcct gccgacgacg agcctggtgc tgggcaagaa ccaaacgctg       1260
gcgaccatca aggccaaaga aaaccagctc tcgcagatcc tcgcacctaa caactattac       1320
cctagcaaga acctggcacc tatcgccctg aatgcccagg acgatttctc cagcaccccg       1380
attacgatga actacaacca gttcctggag ttggaaaaga ccaagcagct gcgcttggac       1440
acggatcaag tttatggcaa catcgccacg tacaactttg agaatggtcg ggtgcgcgtt       1500
gataccggtt ccaattggag cgaagtcctg ccccagatcc aggaaaccac cgcacggatc       1560
atcttcaacg gtaaagacct caacctcgtc gaacgtcgga ttgcagccgt caacccatcc       1620
gacccttttg gagaccacca accggacatg accttgaagg aagcgttgaa gatcgccttc       1680
ggctttaacg aacccaacgg gaacctgcag taccaaggta aggacatcac cgagttcgac       1740
ttcaacttcg accagcagac ctcccaaaac atcaagaatc agttggcgga gctgaacgcc       1800
accaacatct acaccgtcct ggacaagatc aaattgaacg ccaagatgaa catcttgatt       1860
cgcgataagc gttttcacta tgaccgcaac aatatcgccg tgggtgctga cgagagcgtc       1920
gtgaaagaag cccaccgtga agtcatcaac agcagcacgg aaggcctgct cctgaacatt       1980
gataaggata tccgcaagat cctgagcggc tacatcgtcg aaatcgagga taccgaaggc       2040
ctcaaggagg tgatcaacga tcgctacgac atgttgaaca tttcgtccct gcgccaagac       2100
gggaagacct tcatcgactt caagaagtac aacgacaaac tgccgctgta tatctcgaac       2160
ccgaactaca agttaacgt ctatgccgtg accaaggaga acaccatcat caacccctcg        2220
gagaatggcg acacgtcgac caacggcatt aagaagattc tgatcttctc gaagaagggc       2280
tatgagatcg ggcaccatca ccaccatcat tga                                     2313
```

<210> SEQ ID NO 3
<211> LENGTH: 43
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 3
ctactagtag gaggtaactt atggaagtga agcaggagaa tcg                           43

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgctcgagt cattaatgat ggtggtgatg gtgcccgatc tc                            42

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctactagtag gaggtaactt atgtcgacct ccgctgggcc tacgg                         45

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctactagtag gaggtaactt atggagctga acgccaccaa c                            41

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggactagtag gaggtaactt atgaaactga acgtttgat g                             41

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagaaccttg cgcttcttgg ccaccgcgtt ggc                                     33

<210> SEQ ID NO 9
<211> LENGTH: 33
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 9
gccaacgcgg tggccaagaa gcgcaaggtt ctg                                    33

<210> SEQ ID NO 10
<211> LENGTH: 2295
<212> TYPE: DNA
<213> ORGANISM: Artificial Sequence
<220> FEATURE:
<223> OTHER INFORMATION: Description of Artificial Sequence: Synthetic
      optimized rPA

<400> SEQUENCE: 10

```
atgaagaagc gcaaggttct gatcccattg atggccttgt cgaccatcct ggtgtcctcc        60
accggcaatt tggaagtgat ccaggctgaa gtgaagcagg agaatcgcct gctgaacgag       120
tcggagagct cgtcgcaggg cctcctgggc tactactttt cggatttgaa ctttcaggct       180
cccatggtgg tgaccagtag tacgaccggt gacctgtcca tcccgtccag cgaactggaa       240
aacattccgt cggaaaaacca gtacttccaa agcgcgattt ggagcggctt catcaaggtc       300
aagaagtcgg acgaatacac ttttgccacc agcgctgaca ccatgtgac catgtgggtg       360 gatgaccagg aagtcattaa caaggcctcc aacagcaaca aaatccgtct ggagaaaggt       420
cgcttgtatc agatcaaaat ccaataccaa cgcgaaaacc cgacggaaaa gggcttggac       480
ttcaagctgt actggaccga cagccaaaac aagaaggagg tcatctcctc cgacaacctg       540
cagctgcccg agctgaaaca gaagtcgtcg aattcgcgca gaaacggtc gacctccgct       600 gggcctacgg tgccagaccg cgacaacgac ggtatcccccg actcgctgga agttgagggt       660
tatactgtgg atgtcaagaa caagcgtacc ttcctgagcc cctggatctc gaatatccat       720
gagaagaagg gtctcacgaa gtacaagtcc agtcccgaga atggagcac cgcgagcgac       780 ccgtactccg acttcgaaaa ggtcactggc cgtattgata gaacgtttc ccctgaagct       840 cggcatccgt tggttgcagc ctacccgatc gtgcatgttg acatggaaaa cattatcctg       900
agcaagaacg aagaccagag cacccagaat accgactccg aaacccgcac cattagcaag       960
aacacgtcca cgagccgcac ccataccctcg gaggtccacg gtaacgcgga agtgcacgcc      1020
tcgttcttcg atattggtgg gtcggtgtcc gctggtttca gcaactccaa ttcgagcacc      1080
gtcgccatcg accactcgct gtccttggct ggtgagcgca cctgggcaga gaccatgggg      1140
ctgaacaccg cagacaccgc acgtctgaac gcgaatatcc gctacgtgaa caccggcacc      1200
gcacccatct acaacgtcct gccgacgacg agcctggtgc tgggcaagaa ccaaacgctg      1260
gcgaccatca aggccaaaga aaaccagctc tcgcagatcc tcgcacctaa caactattac      1320
cctagcaaga acctggcacc tatcgccctg aatgcccagg acgatttctc cagcaccccg      1380
attacgatga actacaacca gttcctggag ttggaaaaga ccaagcagct gcgcttggac      1440
acggatcaag tttatggcaa catcgccacg tacaactttg agaatggtcg ggtgcgcgtt      1500
gataccggtt ccaattggag cgaagtcctg cccccagatcc aggaaaccac cgcacggatc      1560
atcttcaacg gtaaagacct caacctcgtc gaacgtcgga ttgcagccgt caacccatcc      1620
gaccctttgg agaccaccaa accggacatg accttgaagg aagcgttgaa gatcgccttc      1680
ggctttaacg aacccaacgg gaacctgcag taccaaggta aggacatcac cgagttcgac      1740
ttcaacttcg accagcagac ctcccaaaac atcaagaatc agttggcgga gctgaacgcc      1800
accaacatct acaccgtcct ggacaagatc aaattgaacg ccaagatgaa catcttgatt      1860
```

```
cgcgataagc gttttcacta tgaccgcaac aatatcgccg tgggtgctga cgagagcgtc   1920
gtgaaagaag cccaccgtga agtcatcaac agcagcacgg aaggcctgct cctgaacatt   1980
gataaggata tccgcaagat cctgagcggc tacatcgtcg aaatcgagga taccgaaggc   2040
ctcaaggagg tgatcaacga tcgctacgac atgttgaaca tttcgtccct gcgccaagac   2100
gggaagacct tcatcgactt caagaagtac aacgacaaac tgccgctgta tatctcgaac   2160
ccgaactaca agttaacgt ctatgccgtg accaaggaga acaccatcat caaccccctcg   2220 gagaatggcg acacgtcgac caacggcatt aagaagattc tgatcttctc gaagaagggc   2280
tatgagatcg ggtga                                                    2295

<210> SEQ ID NO 11
<211> LENGTH: 2211
<212> TYPE: DNA
<213> ORGANISM: Artificial Sequence
<220> FEATURE:
<223> OTHER INFORMATION: Description of Artificial Sequence: Synthetic
      optimized rPA

<400> SEQUENCE: 11
atggaagtga agcaggagaa tcgcctgctg aacgagtcgg agagctcgtc gcagggcctc     60
ctgggctact acttttcgga tttgaacttt caggctccca tggtggtgac cagtagtacg    120
accggtgacc tgtccatccc gtccagcgaa ctggaaaaca ttccgtcgga aaaccagtac    180
ttccaaagcg cgatttggag cggcttcatc aaggtcaaga agtcggacga atacactttt    240
gccaccagcg ctgacaacca tgtgaccatg tgggtggatg accaggaagt cattaacaag    300
gcctccaaca gcaacaaaat ccgtctggag aaaggtcgct tgtatcagat caaaatccaa    360
taccaacgcg aaaacccgac ggaaaagggc ttggacttca gctgtactg gaccgacagc    420 caaaacaaga aggaggtcat ctcctccgac aacctgcagc tgcccgagct gaaacagaag    480
tcgtcgaatt cgcgcaagaa acggtcgacc tccgctgggc ctacggtgcc agaccgcgac    540
aacgacggta tccccgactc gctggaagtt gagggttata ctgtggatgt caagaacaag    600
cgtaccttcc tgagccctg gatctcgaat atccatgaga agaagggtct cacgaagtac    660
aagtccagtc ccgagaaatg gagcaccgcg agcgacccgt actccgactt cgaaaaggtc    720
actggccgta ttgataagaa cgttttcccct gaagctcggc atccgttggt tgcagcctac    780
ccgatcgtgc atgttgacat ggaaaacatt atcctgagca agaacgaaga ccagagcacc    840 cagaatccg actccgaaac ccgcaccatt agcaagaaca cgtccacgag ccgcacccat    900
acctcggagg tccacggtaa cgcggaagtg cacgcctcgt tcttcgatat tggtgggtcg    960
gtgtccgctg gtttcagcaa ctccaattcg agcaccgtcg ccatcgacca ctcgctgtcc   1020
ttggctggtg agcgcacctg ggcagagacc atggggctga acaccgcaga caccgcacgt   1080
ctgaacgcga atatccgcta cgtgaacacc ggcaccgcac ccatctacaa cgtcctgccg   1140
acgacgagcc tggtgctggg caagaaccaa acgctggcga ccatcaaggc caagaaaaac   1200
cagctctcgc agatcctcgc acctaacaac tattacccta gcaagaacct ggcacctatc   1260
gccctgaatg cccaggacga tttctccagc accccgatta cgatgaacta caaccagttc   1320
ctggagttgg aaaagaccaa gcagctgcgc ttggacacgg atcaagttta tggcaacatc   1380
gccacgtaca actttgagaa tggtcgggtg cgcgttgata ccggttccaa ttggagcgaa   1440 gtcctgccc agatccagga aaccaccgca cggatcatct tcaacggtaa agacctcaac   1500
ctcgtcgaac gtcggattgc agccgtcaac ccatccgacc ctttggagac caccaaaccg   1560
gacatgacct tgaaggaagc gttgaagatc gccttcggct ttaacgaacc caacgggaac   1620
```

```
ctgcagtacc aaggtaagga catcaccgag ttcgacttca acttcgacca gcagacctcc   1680
caaaacatca agaatcagtt ggcggagctg aacgccacca acatctacac cgtcctggac   1740
aagatcaaat tgaacgccaa gatgaacatc ttgattcgcg ataagcgttt tcactatgac   1800
cgcaacaata tcgccgtggg tgctgacgag agcgtcgtga aagaagccca ccgtgaagtc   1860
atcaacagca gcacggaagg cctgctcctg aacattgata aggatatccg caagatcctg   1920
agcggctaca tcgtcgaaat cgaggatacc gaaggcctca aggaggtgat caacgatcgc   1980
tacgacatgt tgaacatttc gtccctgcgc aagacgggga agaccttcat cgacttcaag   2040
aagtacaacg acaaactgcc gctgtatatc tcgaacccga actacaaagt taacgtctat   2100
gccgtgacca aggagaacac catcatcaac ccctcggaga atggcgacac gtcgaccaac   2160
ggcattaaga agattctgat cttctcgaag aagggctatg agatcgggtg a            2211

<210> SEQ ID NO 12
<211> LENGTH: 2280
<212> TYPE: DNA
<213> ORGANISM: Artificial Sequence
<220> FEATURE:
<223> OTHER INFORMATION: Description of Artificial Sequence: Synthetic
      optimized rPA

<400> SEQUENCE: 12
atgaaactga acgtttgat ggcggcaatg acttttgtcg ctgctggcgt tgcgaccgcc     60
aacgcggtgg ccgaagtgaa gcaggagaat cgcctgctga cgagtcgga gagctcgtcg    120 cagggcctcc tgggctacta cttttcggat ttgaactttc aggctcccat ggtggtgacc    180
agtagtacga ccggtgacct gtccatcccg tccagcgaac tggaaaacat tccgtcggaa    240
aaccagtact tccaaagcgc gatttggagc ggcttcatca aggtcaagaa gtcggacgaa    300
tacacttttg ccaccagcgc tgacaaccat gtgaccatgt gggtggatga ccaggaagtc    360
attaacaagg cctccaacag caacaaaatc cgtctggaga aggtcgcttt gtatcagatc    420
aaaatccaat accaacgcga aaacccgacg gaaaagggct tggacttcaa gctgtactgg    480
accgacagcc aaaacaagaa ggaggtcatc tcctccgaca acctgcagct gcccgagctg    540
aaacagaagt cgtcgaattc gcgcaagaaa cggtcgacct ccgctggggc tacggtgcca    600
gaccgcgaca acgacggtat ccccgactcg ctggaagttg agggttatac tgtggatgtc    660
aagaacaagc gtaccttcct gagccctgg atctcgaata tccatgagaa gaagggtctc    720
acgaagtaca agtccagtcc cgagaaatgg agcaccgcga gcgacccgta ctccgacttc    780
gaaaaggtca ctggccgtat tgataagaac gtttcccctg aagctcggca tccgttggtt    840
gcagcctacc cgatcgtgca tgttgacatg gaaaacatta tcctgagcaa gaacgaagac    900
cagagcaccc agaataccga ctccgaaacc cgcaccatta gcaagaacac gtccacgagc    960
cgcacccata cctcggaggt ccacggtaac gcggaagtgc acgcctcgtt cttcgatatt   1020
ggtgggtcgg tgtccgctgg tttcagcaac tccaattcga gcaccgtcgc catcgaccac   1080
tcgctgtcct ggctggtga gcgcacctgg gcagagacca tggggctgaa caccgcagac   1140
accgcacgtc tgaacgcgaa tatccgctac gtgaacaccg gcaccgcacc catctacaac   1200
gtcctgccga cgacgagcct ggtgctgggc aagaaccaaa cgctggcgac catcaaggcc   1260
aaagaaaacc agctctcgca gatcctcgca cctaacaact attaccctag caagaacctg   1320
gcacctatcg ccctgaatgc ccaggacgat ttctccagca cccgattac gatgaactac   1380 aaccagttcc tggagttgga aaagaccaag cagctgcgct tggacacgga tcaagtttat   1440
```

-continued

```
ggcaacatcg ccacgtacaa ctttgagaat ggtcgggtgc gcgttgatac cggttccaat    1500
tggagcgaag tcctgcccca gatccaggaa accaccgcac ggatcatctt caacggtaaa    1560
gacctcaacc tcgtcgaacg tcggattgca gccgtcaacc catccgaccc tttggagacc    1620
accaaaccgg acatgacctt gaaggaagcg ttgaagatcg ccttcggctt taacgaaccc    1680
aacgggaacc tgcagtacca aggtaaggac atcaccgagt tcgacttcaa cttcgaccag    1740
cagacctccc aaaacatcaa gaatcagttg gcggagctga acgccaccaa catctacacc    1800
gtcctggaca agatcaaatt gaacgccaag atgaacatct tgattcgcga taagcgtttt    1860
cactatgacc gcaacaatat cgccgtgggt gctgacgaga gcgtcgtgaa agaagcccac    1920
cgtgaagtca tcaacagcag cacggaaggc ctgctcctga acattgataa ggatatccgc    1980
aagatcctga gcggctacat cgtcgaaatc gaggataccg aaggcctcaa ggaggtgatc    2040
aacgatcgct acgacatgtt gaacatttcg tccctgcgcc aagacgggaa gaccttcatc    2100
gacttcaaga agtacaacga caaactgccg ctgtatatct cgaacccgaa ctacaaagtt    2160
aacgtctatg ccgtgaccaa ggagaacacc atcatcaacc cctcggagaa tggcgacacg    2220
tcgaccaacg gcattaagaa gattctgatc ttctcgaaga agggctatga gatcgggtga    2280
```

<210> SEQ ID NO 13
<211> LENGTH: 2229
<212> TYPE: DNA
<213> ORGANISM: Artificial Sequence
<220> FEATURE:
<223> OTHER INFORMATION: Description of Artificial Sequence: Synthetic
      optimized rPA

<400> SEQUENCE: 13

```
atggaagtga agcaggagaa tcgcctgctg aacgagtcgg agagctcgtc gcagggcctc      60
ctgggctact acttttcgga tttgaacttt caggctccca tggtggtgac cagtagtacg     120
accggtgacc tgtccatccc gtccagcgaa ctggaaaaca ttccgtcgga aaaccagtac     180
ttccaaagcg cgatttggag cggcttcatc aaggtcaaga agtcggacga atacactttt     240
gccaccagcg ctgacaacca tgtgaccatg tgggtggatg accaggaagt cattaacaag     300
gcctccaaca gcaacaaaat ccgtctggag aaaggtcgct tgtatcagat caaaatccaa     360
taccaacgcg aaaacccgac ggaaaagggc ttggacttca gctgtactg gaccgacagc     420 caaaacaaga aggaggtcat ctcctccgac aacctgcagc tgcccgagct gaaacagaag     480
tcgtcgaatt cgcgcaagaa acggtcgacc tccgctgggc ctacggtgcc agaccgcgac     540
aacgacggta tccccgactc gctggaagtt gagggttata ctgtggatgt caagaacaag     600
cgtaccttcc tgagccctg gatctcgaat atccatgaga agaagggtct cacgaagtac     660
aagtccagtc ccgagaaatg gagcaccgcg agcgacccgt actccgactt cgaaaaggtc     720
actggccgta ttgataagaa cgtttcccct gaagctcggc atccgttggt tgcagcctac     780
ccgatcgtgc atgttgacat ggaaaacatt atcctgagca gaacgaaga ccagagcacc     840 cagaataccg actccgaaac ccgcaccatt agcaagaaca cgtccacgag ccgcacccat     900
acctcggagg tccacggtaa cgcggaagtg cacgcctcgt tcttcgatat tggtgggtcg     960
gtgtccgctg gtttcagcaa ctccaattcg agcaccgtcg ccatcgacca ctcgctgtcc    1020
ttggctggtg agcgcacctg ggcagagacc atggggctga acaccgcaga caccgcacgt    1080
ctgaacgcga atatccgcta cgtgaacacc ggcaccgcac ccatctacaa cgtcctgccg    1140
acgacgagcc tggtgctggg caagaaccaa acgctggcga ccatcaaggc caagaaaaac    1200
cagctctcgc agatcctcgc acctaacaac tattacccta gcaagaacct ggcacctatc    1260
```

| | |
|---|---|
| gccctgaatg cccaggacga tttctccagc accccgatta cgatgaacta caaccagttc | 1320 |
| ctggagttgg aaaagaccaa gcagctgcgc ttggacacgg atcaagttta tggcaacatc | 1380 |
| gccacgtaca actttgagaa tggtcgggtg cgcgttgata ccggttccaa ttggagcgaa | 1440 |
| gtcctgcccc agatccagga aaccaccgca cggatcatct tcaacggtaa agacctcaac | 1500 |
| ctcgtcgaac gtcggattgc agccgtcaac ccatccgacc ctttggagac caccaaaccg | 1560 |
| gacatgacct tgaaggaagc gttgaagatc gccttcggct taacgaacc caacgggaac | 1620 |
| ctgcagtacc aagtaagga catcaccgag ttcgacttca acttcgacca gcagacctcc | 1680 |
| caaaacatca gaatcagtt ggcggagctg aacgccacca catctacac cgtcctggac | 1740 |
| aagatcaaat tgaacgccaa gatgaacatc ttgattcgcg ataagcgttt tcactatgac | 1800 |
| cgcaacaata tcgccgtggg tgctgacgag agcgtcgtga agaagcccca ccgtgaagtc | 1860 |
| atcaacagca gcacggaagg cctgctcctg aacattgata aggatatccg caagatcctg | 1920 |
| agcggctaca tcgtcgaaat cgaggatacc gaaggcctca aggaggtgat caacgatcgc | 1980 |
| tacgacatgt tgaacatttc gtccctgcgc caagacggga agaccttcat cgacttcaag | 2040 |
| aagtacaacg caaactgcc gctgtatatc tcgaacccga actacaaagt taacgtctat | 2100 |
| gccgtgacca aggagaacac catcatcaac ccctcggaga atggcgacac gtcgaccaac | 2160 |
| ggcattaaga agattctgat cttctcgaag aagggctatg agatcgggca ccatcaccac | 2220 |
| catcattga | 2229 |

<210> SEQ ID NO 14
<211> LENGTH: 1728
<212> TYPE: DNA
<213> ORGANISM: Artificial Sequence
<220> FEATURE:
<223> OTHER INFORMATION: Description of Artificial Sequence: Synthetic optimized rPA

<400> SEQUENCE: 14

| | |
|---|---|
| atgtcgacct ccgctgggcc tacggtgcca gaccgcgaca cgacggtat ccccgactcg | 60 |
| ctggaagttg agggttatac tgtggatgtc aagaacaagc gtaccttcct gagcccctgg | 120 |
| atctcgaata tccatgagaa gaagggtctc acgaagtaca agtccagtcc gagaaatgg | 180 |
| agcaccgcga gcgacccgta ctccgacttc gaaaaggtca ctggccgtat tgataagaac | 240 |
| gtttccctg aagctcggca tccgttggtt gcagcctacc cgatcgtgca tgttgacatg | 300 |
| gaaaacatta tcctgagcaa gaacgaagac cagagcaccc agaataccga ctccgaaacc | 360 |
| cgcaccatta gcaagaacac gtccacgagc cgcacccata cctcggaggt ccacggtaac | 420 |
| gcggaagtgc acgcctcgtt cttcgatatt ggtgggtcgg tgtccgctgg tttcagcaac | 480 |
| tccaattcga gcaccgtcgc catcgaccac tcgctgtcct ggctggtga gcgcacctgg | 540 |
| gcagagacca tggggctgaa caccgcagac accgcacgtc tgaacgcgaa atccgctac | 600 |
| gtgaacaccg gcaccgcacc catctacaac gtcctgccga cgacgagcct ggtgctgggc | 660 |
| aagaaccaaa gctggcgac catcaaggcc aaagaaaacc agctctcgca gatcctcgca | 720 |
| cctaacaact attaccctag caagaacctg gcacctatcg ccctgaatgc ccaggacgat | 780 |
| ttctccagca ccccgattac gatgaactac aaccagttcc tggagttgga aaagaccaag | 840 |
| cagctgcgct tggacacgga tcaagtttat ggcaacatcg ccacgtacaa ctttgagaat | 900 |
| ggtcgggtgc gcgttgatac cggttccaat tggagcgaag tcctgcccca gatccaggaa | 960 |
| accaccgcac ggatcatctt caacggtaaa gacctcaacc tcgtcgaacg tcggattgca | 1020 |

```
gccgtcaacc catccgaccc tttggagacc accaaaccgg acatgacctt gaaggaagcg    1080
ttgaagatcg ccttcggctt taacgaaccc aacgggaacc tgcagtacca aggtaaggac    1140
atcaccgagt tcgacttcaa cttcgaccag cagacctccc aaaacatcaa gaatcagttg    1200
gcggagctga acgccaccaa catctacacc gtcctggaca agatcaaatt gaacgccaag    1260
atgaacatct tgattcgcga taagcgtttt cactatgacc gcaacaatat cgccgtgggt    1320
gctgacgaga gcgtcgtgaa agaagcccac cgtgaagtca tcaacagcag cacggaaggc    1380
ctgctcctga acattgataa ggatatccgc aagatcctga gcggctacat cgtcgaaatc    1440
gaggataccg aaggcctcaa ggaggtgatc aacgatcgct acgacatgtt gaacatttcg    1500
tccctgcgcc aagacgggaa gaccttcatc gacttcaaga agtacaacga caaactgccg    1560
ctgtatatct cgaaccccga ctacaaagtt aacgtctatg ccgtgaccaa ggagaacacc    1620
atcatcaacc cctcggagaa tggcgacacg tcgaccaacg gcattaagaa gattctgatc    1680
ttctcgaaga agggctatga gatcgggcac catcaccacc atcattga                1728

<210> SEQ ID NO 15
<211> LENGTH: 528
<212> TYPE: DNA
<213> ORGANISM: Artificial Sequence
<220> FEATURE:
<223> OTHER INFORMATION: Description of Artificial Sequence: Synthetic
      optimized rPA

<400> SEQUENCE: 15
atggagctga acgccaccaa catctacacc gtcctggaca agatcaaatt gaacgccaag      60
atgaacatct tgattcgcga taagcgtttt cactatgacc gcaacaatat cgccgtgggt     120
gctgacgaga gcgtcgtgaa agaagcccac cgtgaagtca tcaacagcag cacggaaggc     180
ctgctcctga acattgataa ggatatccgc aagatcctga gcggctacat cgtcgaaatc     240
gaggataccg aaggcctcaa ggaggtgatc aacgatcgct acgacatgtt gaacatttcg     300
tccctgcgcc aagacgggaa gaccttcatc gacttcaaga agtacaacga caaactgccg     360
ctgtatatct cgaaccccga ctacaaagtt aacgtctatg ccgtgaccaa ggagaacacc     420
atcatcaacc cctcggagaa tggcgacacg tcgaccaacg gcattaagaa gattctgatc     480
ttctcgaaga agggctatga gatcgggcac catcaccacc atcattga                  528

<210> SEQ ID NO 16
<211> LENGTH: 2309
<212> TYPE: DNA
<213> ORGANISM: Artificial Sequence
<220> FEATURE:
<223> OTHER INFORMATION: Description of Artificial Sequence: Synthetic
      optimized rPA83 version 1

<400> SEQUENCE: 16
atgaagaaac gcaaagtcct gattcctctg atggccctgt ccaccatcct ggtcagcagc      60
accgggaacc tggaagtcat tcaggccgag gtgaagcagg agaatcgcct gctgaacgag     120
tccgagtcga gcagccaggg tctgctggcc tactacttca gcgatctgaa ctttcaagcc     180
ccgatggtcg tgaccagctc gaccaccggc gatctgtcga tcccgagctc ggagctggaa     240
aacatcccca gcgaaaacca gtacttccag agcgctatct ggagcggctt catcaaggtg     300
aagaagtcgg atgaatatac ctttgccacc tcggccgaca accacgttac tatgtgggtc     360
gatgatcaag aagtgatcaa caaggcctcc aatagcaaca aaatccgtct ggagaagggg     420
cgtctgtatc aaatcaagat ccaataccaa cgcgaaaacc cgacggaaaa aggtctggac     480
```

```
ttcaagctgt actggaccga ttcccagaac aagaaggaag tgatcagctc cgacaatctg      540
cagttgccgg aactgaagca gaagagttcg aacagccgta aaaagcgctc cacctcggct      600
ggccctaccg tccccgaccg tgacaacgac ggcatcccag attccctgga ggttgaaggc      660
tacaccgtgg acgttaagaa taagcgcacc ttcctgtcgc cctggatctc gaacatccat      720
gagaagaaag gcctgaccaa gtataagtcg agtcccgaga gtggagcac  cgcgagcgac      780 ccgtattccg atttcgaaaa ggtgactggc cgcatcgaca gaacgtgtc  gccagaagct      840 cgccacccgc tggtcgcggc ctacccgatt gtgcatgtgg acatggaaaa cattattctc      900
agtaagaatg aagaccagag tacccagaat accgactccg aaacccgcac catcagcaag      960
aataccagca cgagtcgcac gcacacgtcc gaagtgcacg gcaacgcaga gtccacgca     1020 tccttcttcg atatcggtgg ttcggtgtcc gcaggcttta gcaattcgaa tagcagcacc     1080
gtggccattg accattcctt gagcctggcg ggcgaacgca cctgggccga accatgggc     1140 ctcaacaccg cggacacggc acgcctgaac gccaacattc gctatgtgaa caccggcacc     1200
gccccgattt acaacgtgct gcctacgact agcctggtgc tcggcaagaa tcagacgttg     1260
gccacgatca aggccaagga aaaccagttg tcgcaaattc tcgcacctaa caattactat     1320
ccgagtaaga acctggcccc gatcgccctg aacgcccagg acgacttctc cagcacgcct     1380
atcaccatga actacaacca gttcctggag ctggagaaaa ccaagcaact gcgtctggac     1440
acggaccagg tgtacggcaa cattgcgacg tacaatttcg agaacgggcg cgttcgggtt     1500
gataccggtt cgaactggtc ggaagtcctg ccccaaatcc aggaaaccac ggcgcgcatt     1560 atttttcaacg gtaaagacct gaacttggtc gaacgccgca tcgccgcagt caacccgtcc     1620
gaccctttgg agacgaccaa accggacatg accctgaagg aagccctgaa gatcgccttc     1680
ggcttcaacg agccgaatgg taacctgcaa tatcagggca aggacatcac cgagttcgac     1740
tttaacttcg atcagcagac gtcgcagaat atcaagaacc agctggcgga attgaatgcc     1800
actaacattt acaccgtgtt ggacaagatc aagctgaacg ctaagatgaa cattctgatc     1860
cgtgacaaac gcttccatta cgaccgcaac aacatcgcgg tgggcgctga cgaatcggtg     1920
gtgaaagagg cccaccgcga ggttatcaac agctcgaccg agggcttgct gctgaatatc     1980
gacaaagaca tccgcaagat cttgtccggc tacatcgtgg aaatcgaaga caccgagggg     2040
ttgaaagaag tcatcaacga ccgttacgac atgctcaaca tcagtagcct gcgccaggac     2100
gggaagacct tcattgattt taagaaatac aacgataagc tgccccctgta cattagcaac     2160 ccgaactaca aggtcaatgt ctacgcggtt acgaaggaaa acaccatcat taaccccgtcc     2220 gagaacggcg acacctcgac gaacggcatc aagaagattc tgatcttcag taagaaaggg     2280
tacgaaatcg gctgataata gctcgagcg                                       2309
```

<210> SEQ ID NO 17
<211> LENGTH: 2309
<212> TYPE: DNA
<213> ORGANISM: Artificial Sequence
<220> FEATURE:
<223> OTHER INFORMATION: Description of Artificial Sequence: Synthetic
      optimized rPA83 version 2

<400> SEQUENCE: 17

```
atgaaaaagc gtaaagttct gattccgctg atggccctct cgactatcct ggtcagctcc       60
accggcaacc tggaagtcat ccaggctgaa gtcaagcagg aaaatcgtct gctcaatgaa      120
agcgaatcgt ccagccaagg gctgttgggt tactacttca gcgacctgaa cttccaggct      180
cctatggtcg tgaccagcag taccactggt gacctgtcga tccctcgtc  cgagctggaa      240
```

```
aatatcccat cggaaaacca gtattttcag agcgctatct ggagcggttt catcaaggtg    300
aaaaagagcg atgaatatac cttcgccacc tcggcggaca atcacgtcac catgtgggtg    360
gatgaccaag aagtcattaa taaggcgtcg aacagtaaca aaatccgtct ggagaagggc    420
cgcctgtacc agatcaagat ccagtaccag cgcgagaacc ctacggaaaa gggcctggac    480
tttaagctgt attggacgga ttcgcaaaac aagaaagaag tgatcagcag cgacaacctg    540
cagctgccgg aactcaagca aaagagctcg aacagccgca agaagcgttc caccagcgct    600
ggcccgaccg tgccggaccg cgacaacgat ggcatcccgg acagcttgga agtcgagggc    660
tacacggtgg atgtcaagaa caaacgcacg ttcctcagtc cgtggatcag caacattcat    720
gaaaagaaag gcttgaccaa atacaagagt agcccggaga gtggtccac cgcaagcgat    780 ccatactcgg atttcgagaa agttacgggc cgcattgaca agaacgtgag cccggaagcc    840
cgtcatccgc tggtggcggc atacccgatt gtgcatgtgg atatgaaaa tatcatcctg    900 agtaaaaacg aggaccaaag tacccagaac acggacagcg aaacccgcac catctcgaag    960
aacaccagta cctcgcgtac ccacacgtcg gaagtccacg gcaacgccga agtgcatgcc    1020 agcttttcg atatcggcgg gagcgtgtcg gccggcttct cgaattcgaa ctcgtccacc    1080
gttgccatcg accattcctt gagcctggca ggcgaacgca cgtgggcgga aaccatgggg    1140
ttgaacacgg ccgacacggc ccgtttgaac gccaacatcc gctatgtgaa caccggtacc    1200
gctcccatct ataacgtgtt gccgaccact tcgctggtgt tgggtaaaaa ccagaccctg    1260
gcgaccatca aggctaagga gaaccagctc agtcaaatcc tggccccgaa caactactac    1320
ccaagcaaaa acttggcccc gatcgcactc aacgcccagg atgacttctc cagcacccct    1380
atcaccatga actacaacca gtttctggag ctcgaaaaga ctaaacaact gcgcctcgac    1440
accgatcaag tgtatggcaa catcgcgacg tataacttcg aaaatggccg cgtgcgcgtg    1500
gacaccggca gcaactggtc ggaagtcttg ccgcagatcc aggaaaccac cgcgcggatc    1560
atctttaatg ggaaggacct gaacctggtc gagcgccgta tcgccgcagt gaacccgtcc    1620
gaccctctgg aaaccaccaa gcccgacatg acgctcaaag aggccctcaa gatcgccttt    1680
ggcttcaatg aaccgaacgg taacttgcag taccagggta agacattac cgagtttgac    1740 ttcaacttcg atcagcaaac cagccagaat atcaaaaacc agctggcgga gctgaatgcc    1800
acgaacatct acacggtctt ggacaagatc aagctcaacg cgaagatgaa cattctcatt    1860
cgcgacaagc gcttccatta tgaccgtaac aacattgctg ttggtgccga cgaatccgtg    1920
gtcaaggaag cccatcgcga ggtcattaat agcagcactg agggtttgct gctgaacatc    1980
gacaaagata tccggaaaat cctctccggc tatatcgtcg aaatcgaaga cacgaaggt    2040 ttgaaagaag ttatcaacga ccgctacgac atgctgaaca tttcgagcct gcggcaggac    2100
gggaaaacct tcatcgattt caagaagtac aatgacaaat tgccgctgta catcagcaac    2160
cctaactaca aggtgaacgt gtacgcagtc accaaggaga acacgatcat caaccttcg    2220 gaaaatgggg acacgtccac taacggtatc aaaaagatcc tgattttctc gaagaagggc    2280
tacgaaatcg gctgataata gctcgagcg                                    2309
```

<210> SEQ ID NO 18
<211> LENGTH: 2308
<212> TYPE: DNA
<213> ORGANISM: Artificial Sequence
<220> FEATURE:
<223> OTHER INFORMATION: Description of Artificial Sequence: Synthetic
   optimized rPA83 version 3

-continued

```
<400> SEQUENCE: 18
atgaagaaac gtaaggtcct gatcccactg atggctttgt ccactatcct ggtgagctcg      60
accggcaacc tggaagtgat ccaagccgaa gtgaagcaag agaatcggct gttgaacgag     120
tccgaatcga gttcgcaggg cctgctgggc tactacttca gcgacctgaa ctttcaggct     180
ccgatggtcg tcaccagcag cactaccggc gatctctcca tcccgtcctc cgaactggag     240
aatatcccct ccgagaacca gtattttcag agcgccattt ggtcgggttt catcaaggtc     300
aagaagagcg acgagtacac ctttgcgact tcggcagaca accatgtgac catgtgggtg     360
gacgaccaag aagtcatcaa caaggcgagt aacagcaaca aaatccgctt ggagaagggc     420
cggttgtacc aaatcaaaat ccagtaccag cgtgaaaacc ctaccgaaaa gggcttggac     480
ttcaagctgt actggaccga cagccagaac aaaaaggaag tcatcagctc cgataatctc     540
cagctgccag aactgaagca aaagagctcg aacagccgca agaaacgcag cacgtcggcg     600
ggtcctacgg tcccagatcg cgacaacgat gggatcccag acagcctgga ggtggaaggc     660
tacaccgtcg atgtcaaaaa caaacggacc tttctcagcc cttggattag caacatccac     720
gaaaagaaag gcctgacgaa atacaaaagc agcccggaga gtggagtac cgcgtccgat     780 ccatactcgg acttcgagaa agtgaccggg cgcattgaca aaaacgtgtc gccggaagcc     840
cgccacccgc tggtcgccgc gtacccgatc gtccatgtcg atatggaaaa catcatcctg     900
agcaagaacg aagatcaatc gacgcagaac accgacagcg aaacccgtac catctcccaa     960
aacaccagca cttcgcgtac tcacaccagc gaagtccacg gtaacgcgga agtccatgca    1020
agtttctttg acatcggcgg tagtgtgtcg gccgggttca gcaacagcaa tagtagtacc    1080
gtggctattg accatagcct gtcgttggcg ggcgagcgta cgtgggcgga accatgggc    1140 ctcaacaccg ctgacacggc gcggttgaac gcgaacatcc gctacgtcaa cacgggcacg    1200
gccccgatct ataatgtcct gcccaccacc agcctggtgc tcggtaaaaa ccagacgctg    1260
gccaccatca aggcgaagga gaaccagttg tcgcagatct tggccccgaa taactattat    1320
cccagcaaga acctggcgcc catcgcactg aatgcgcagg acgacttcag cagtacgccc    1380
atcaccatga attacaacca gttcctggag ctggagaaaa cgaaacagtt gcggctggac    1440
accgatcagg tttacggtaa tattgccacc tacaattttg aaaacgggcg ggtgcgcgtc    1500
gatacgggca gtaactggag cgaagtcctg ccccagatcc aagaaccac cgcgcgcatc    1560 atctttaacg gcaaggacct gaatctggtc gaacgccgca ttgcggcggt taacccatcg    1620 gacccctttgg aaaccaccaa gccggatatg accttgaaag aggccttgaa gatcgctttt    1680
ggtttcaacg agccgaacgg caacctgcaa taccaaggca agatatcac cgaattcgac    1740 ttcaactttg accaacagac ctcgcaaaac atcaaaaacc agttggccga gttgaacgcc    1800
accaacatct acaccgtgct ggataagatt aagctgaatg cgaagatgaa tatcctcatc    1860
cgcgataagc gctttcatta cgaccgcaac aacatcgccg tcggggccga cgaatcggtc    1920
gtgaaggaag cccatcgcga ggttattaac agcagcacgg aaggcctgtt gctgaatatc    1980
gataaggaca tccgcaaaat tctgtcgggc tacatcgtgg agatcgagga caccgagggc    2040
ctgaaagaag tgatcaacga ccgctacgac atgctcaaca tcagcagctt gcggcaggac    2100
ggtaagacct ttattgactt caagaagtac aatgacaaac tgcccttgta catctccaac    2160
cccaactata aagtgaacgt gtacgccgtg acgaaggaaa acacgatcat taaccccagc    2220
gagaacggcg atacgagcac gaacggcatc aagaagatct tgatcttttc caaaagggc    2280 tatgagatcg gctgataata gctcgagc                                      2308
```

<210> SEQ ID NO 19
<211> LENGTH: 29
<212> TYPE: PRT
<213> ORGANISM: Bacillus anthracis

<400> SEQUENCE: 19

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala
            20                  25

<210> SEQ ID NO 20
<211> LENGTH: 735
<212> TYPE: PRT
<213> ORGANISM: Bacillus anthracis

<400> SEQUENCE: 20

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val

```
            305                 310                 315                 320
Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
                340                 345                 350

Asn Thr Ala Asp Thr Ala Arg Leu Asn Ala Asn Ile Arg Tyr Val Asn
                355                 360                 365

Thr Gly Thr Ala Pro Ile Tyr Asn Val Leu Pro Thr Thr Ser Leu Val
370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
                420                 425                 430

Thr Met Asn Tyr Asn Gln Phe Leu Glu Leu Glu Lys Thr Lys Gln Leu
                435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
                500                 505                 510

Pro Leu Glu Thr Thr Lys Pro Asp Met Thr Leu Lys Glu Ala Leu Lys
                515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
                580                 585                 590

Asp Lys Arg Phe His Tyr Asp Arg Asn Asn Ile Ala Val Gly Ala Asp
                595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
                660                 665                 670

Lys Thr Phe Ile Asp Phe Lys Lys Tyr Asn Asp Lys Leu Pro Leu Tyr
                675                 680                 685

Ile Ser Asn Pro Asn Tyr Lys Val Asn Val Tyr Ala Val Thr Lys Glu
                690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735
```